US007645992B2

(12) United States Patent
Lyubchik et al.

(10) Patent No.: US 7,645,992 B2
(45) Date of Patent: Jan. 12, 2010

(54) NON-INVASIVE METHOD TO IDENTIFY HIDDEN FOREIGN OBJECTS NEAR A HUMAN SUBJECT

(75) Inventors: Yaakov Lyubchik, Kiriat Ekron (IL); Yafim Smoliak, Kiriat Ono (IL); Nathan Blaunshtein, Beer Sheva (IL)

(73) Assignee: Passive Medical Systems Engineering Ltd., Tel-Aviv (IL)

( * ) Notice: Subject to any disclaimer, the term of this patent is extended or adjusted under 35 U.S.C. 154(b) by 386 days.

(21) Appl. No.: 11/426,586

(22) Filed: Jun. 27, 2006

(65) Prior Publication Data

US 2008/0185525 A1   Aug. 7, 2008

Related U.S. Application Data

(60) Provisional application No. 60/694,238, filed on Jun. 28, 2005, provisional application No. 60/708,389, filed on Aug. 16, 2005.

(51) Int. Cl.
*G01J 5/02* (2006.01)
(52) U.S. Cl. .................................................... 250/342
(58) Field of Classification Search ................. 250/342, 250/339.14
See application file for complete search history.

(56) References Cited

U.S. PATENT DOCUMENTS

| 7,010,455 B2 * | 3/2006 | Pieragostini ................ 702/134 |
| 7,238,940 B1 * | 7/2007 | Davidson et al. ............ 250/330 |
| 2005/0110672 A1 * | 5/2005 | Cardiasmenos et al. ....... 342/27 |

* cited by examiner

*Primary Examiner*—David P Porta
*Assistant Examiner*—Marcus H Taningco
(74) *Attorney, Agent, or Firm*—Mark M. Friedman

(57) ABSTRACT

A method and device are revealed to non-invasively identify hidden foreign objects in proximity of living tissue. More specifically to a method and device find a foreign object hidden under the clothes of a person by measuring an anomaly in an infrared radiation signal emitted by the human subject; the anomaly caused by the presence of the foreign object. A spectral scan at the identified location is used to identify the object. Even when the object is hidden behind clothes, the object is positively identified based on the interaction of optical radiation naturally emitted by the human body in the infrared frequency spectrum with every component of the examined object.

13 Claims, 16 Drawing Sheets

NON-INVASIVE METHOD TO IDENTIFY HIDDEN FOREIGN OBJECTS NEAR A HUMAN SUBJECT

This is a continuation-in-part of U.S. Provisional Patent Application No. 60/694,238, filed Jun. 28, 2005 AND 60/708,389 filed Aug. 16, 2005.

FIELD AND BACKGROUND OF THE INVENTION

The present invention relates to a method and device to non-invasively identify hidden foreign objects in proximity of living tissue and more specifically to a method and device that to detect and identify foreign objects hidden under the clothes of a person by measuring an infrared radiation signal emitted by the human subject and by measuring a change in the radiation signal caused by the presence of the foreign object.

The present invention is in the class of methods for structural analysis of multi-component materials. The particular multi-component structures/materials of interest include the following components: a human body (living tissue), clothes, and a foreign object that is composed one or more materials and may include metal, magnetic materials, conductive materials or dielectric materials. Even when the object is hidden behind clothes, the object is positively identified based on the interaction of optical radiation naturally emitted by the human body in the infrared frequency spectrum with every component of the examined object. In addition, magnetic metal detection and reflected light in the infrared (IR), Ultraviolet (UV) or visible spectrums may be employed to supplement identification based on the IR regime.

A living person emits radiation on a wide band of wavelengths. For example, due to its elevated temperature, a human body emits black body radiation in the infrared spectrum. Also the human body reflects radiation in different wavelengths to different degrees. When a foreign object is in proximity of a person, the object affects the radiation field around the person. By sensing anomalies in the radiation field around a person, the present invention detects the presence of foreign objects in proximity to the person including objects hidden behind clothing. Based on the location (including position, as well as shape and size [geometry] of the object) and based on the frequency dependent signature of the radiation anomaly caused by the object, the present invention identifies the foreign object.

There is currently great interest in technologies to quickly detect and identify foreign objects in and around people in a safe, non-intrusive manner. Some important applications of such technologies are detection of weapons and explosives to prevent terrorist attacks and detection of illegal substances by police or customs agents.

Detectors are used to identify and exclude dangerous objects from high security zones (for example the boarding areas of civilian aircraft). Also customs, and drug enforcement agencies use detectors to identify foreign substances hidden in or around the body of a person. Currently popular detectors are metal detectors and x-ray scanners.

X-ray and microwave (penetrating radar) scanners are capable of giving high-resolution pictures of hidden objects. The pictures can be used to positively identify dangerous objects and benign objects. This allows efficient screening so that threats can be detected quickly and with a high reliability without requiring lengthy examinations. Unfortunately, x-rays and microwaves radiation have the drawback that they are active methodologies requiring exposing objects to high-energy beams of x-ray or microwave radiation. These x-ray and microwave beams are dangerous to people and cannot be used for scanning objects on or near living humans.

Metal detectors are safe for use in the vicinity of humans but suffer from two drawbacks. First metal detectors only identify one particular class of dangerous object (those made of metal) but cannot identify other dangerous objects (such as organic explosives, plastic or ceramic weapons, various toxic substances or biological agents). Furthermore, metal detectors are non-specific and cannot differentiate between weapons and benign metal objects of common occurrence (e.g. coins, surgical implants, keys, electronic devices, buttons, zippers) Therefore, where metal detectors are used, a (sometimes lengthy) secondary screening is necessary to preclude non-metallic threats and to determine the nature of detected metal objects. Secondary screening may require intrusive methods such as opening and searching personal baggage, removal of shoes hats or religious apparel and even in some cases strip searches. Such intrusive methods are time consuming, inconvenient, may lead to conflict between security personnel and the public. Reliable routine security systems based on such methodologies are extremely expensive and problem prone.

Currently there is interest in developing scanners to non-intrusively detect a large class of dangerous or illegal substances. One method currently under development detects infrared (IR) radiation naturally emitted by a human body and reveals a hidden object by detecting the disturbance caused by the object in the IR radiation field around a person. Current technologies are based on the integral method of IR-thermal analysis. The integral method consists of the following steps:

1) Measure of the space distribution of the integral heat flow from the object most often from the open surface of the body.

2) Reveal and outline anomalies of the heat flow.

3) Calculate the temperature of the surface sections of the analyzed structure.

A wide class of the thermograph devices and systems (e.g. thermo vision [FLIR], thermal cameras, thermographs, radiometers) use the integral mode of thermograph (IR) analysis to detect and map objects. The aim of this method is the structural analysis of the spatial distribution of the flows (usually from narrow bands of IR radiation within the range of 5 μm-14 μm) from the object and mapping the values of thermodynamic temperature of the structure surface. Under certain conditions, the integral method of IR-thermograph analysis may also be used for detecting the presence of foreign objects (metallic or non-metallic) hidden inside clothes by measuring an anomaly of the heat flow. The use of previous art technology for thermal imaging of heat flows to detect hidden objects has the following technical difficulties and limitations:

1) The integral method doesn't allow classification of the substances of which the foreign object is composed. Thus, with previous art integral methodologies, it is possible to detect the foreign object producing the heat flow anomaly, but it is often impossible to identify the detected object.

2) Previous art integral methodologies (e.g. thermal imaging), detect the integral heat flow and its spatial distribution along the surface of the investigated structure without taking into account the difference between radiant characteristics of structural components. Components having different radiant properties and different temperatures may produce the same values of integral heat flow in the wavelength being measured. Therefore, some foreign objects cannot be detected by previous art integral methodologies. Similarly, a homogeneous surface having surface temperature gradient, can give a signal like that of a foreign object.

3) The wavelength range of IR rays used in previous art integral detectors (from 3-5 μm for thermal cameras or 10-14 μm for FLIRs), are absorbed to a considerable extent by clothes. Therefore, previous art integral mode detectors are not well suited for detecting foreign objects hidden under clothes.

There is thus a widely recognized need for, and it would be highly advantageous to have, a non-intrusive detector that is safe to use in the presence of people and can positively identify a variety of dangerous objects hidden behind clothing and quickly and reliably distinguish dangerous objects and dangerous substances from benign objects.

The present invention solves the above limitations because the present invention detects the presence of anomalies in radiation over a wide frequency band. Thus, even when some radiation bands are blocked by clothing or masked by temperature differentials, the signature of the foreign object on the remaining bands will be detected. Furthermore, the present invention teaches measuring radiation using a differential measure of radiation intensity. A differential measure (for example intensity contrast) quantifies the difference between measured values. An absolute measure (for example heat flow) quantifies measured values directly. The use of a differential measure of radiation intensity (e.g. contrast in radiation intensity) makes the present invention more sensitive to subtle anomalies in radiation than previous art methodologies based on absolute measures of radiation intensity (e.g. thermal imaging using a FLIR or a thermal camera). The advantages of using contrast to detect anomalies in radiation is set forth in A. T. Nesmyanovich, V. N. Ivchenko, G. P. Milinevsky, "Television system for observation of artificial aurora in the conjugate region during ARAKS experiments", Space Sci. Instrument, vol. 4, 1978, pp 251-252; and in N. D Filipp, V. N. Oraevskii, N. Sh. Blaunshtein, and Yu. Ya. Ruzhin, Evolution of Artificial Plasma Formation in The Earth's Ionosphere, Kishinev: Shtiintsa, 1986, 246 pages, which are incorporated by reference for all purposes as if fully set forth herein. Finally, the present invention combines information from the integral analysis of radiation with spectral analysis and other inputs to positively identify foreign objects.

Thus, the present invention provides reliable way of detecting, revealing the exact location, the size and form, and identifying the substance of a foreign object hidden under clothes on a human body. This then aids security personal guaranteeing security of transport, sensitive structures or individuals. It also aids in industrial or military security, criminal investigations, control of illegal substances, and custom control of import and export.

SUMMARY OF THE INVENTION

The present invention is a method and device to non-invasively detect and identify a hidden foreign object in proximity of living tissue. More particularly, the present invention is a method and device to detect and identify a foreign object hidden under the clothes of a human subject by measuring an infrared radiation signal emitted by the subject and by measuring a change in the radiation signal, which is caused by the presence of the foreign object.

According to the teachings of the present invention there is provided a method for identifying a foreign object in proximity to living tissue. The method includes the step of finding a location of an anomaly caused by the foreign object in a radiation emitted by the living tissue. The method further includes the steps of performing a spectral analysis of a signal emanated from the location of the anomaly, and identifying the foreign object based on the location and the results of the spectral analysis.

According to the teachings of the present invention, there is also provided a detector for identifying a foreign object in proximity to living tissue. The detector includes a first sensor assembly sensitive to a first frequency band. The first sensor assembly is configured to find a location of an anomaly in a radiation emitted by the living tissue and to enumerate a characteristic of the anomaly. The foreign object causes the anomaly. The detector also includes a second sensor assembly configured to be sensitive to a second frequency band and a processor configured to identify the foreign object. Identification of the foreign object by the processor is based on the location of the anomaly the characteristic of the anomaly and a difference between an unmodified radiation signal emitted by the human tissue and a second radiation signal scanned at the location of the anomaly. Both the unmodified signal and the second signal are in the second frequency band and both signals are detected by the second sensor assembly. The unmodified signal is the radiation signal emitted by the living tissue and unmodified by the foreign object and the second signal is modified by the foreign object.

According to further features in preferred embodiments of the invention described below, the anomaly is found in radiation including energy in the infrared frequency band.

According to still further features in the described preferred embodiments, the first frequency band of the radiation includes a wide range of wavelengths spanning from a minimum wavelength of less than 5 μm till a maximum wavelength of greater than 12 μm.

According to still further features in the described preferred embodiments, the anomaly is found in a frequency band of the radiation including energy in a first infrared frequency band in the near infrared spectrum of wavelength less than 5 μm and also including energy in a second frequency band in the medium infrared spectrum of wavelength greater than 12 μm.

According to still further features in the described preferred embodiments, the method of identifying a foreign object further includes the step of calculating a differential measure to quantify radiation at the current position of scanning.

According to still further features in the described preferred embodiments, the radiation is characterized by a differential measure that quantifies the difference between a background radiation and a radiation at the current position being scanned.

According to still further features in the described preferred embodiments, the differential measure that quantifies radiation at the current position of scanning is a contrast.

According to still further features in the described preferred embodiments, the method of identifying a foreign object further includes the steps of classifying the foreign object to a general category based on a characteristic of the anomaly in the radiation field, and adapting the spectral analysis to distinguish amongst objects in the general category.

According to still further features in the described preferred embodiments, the foreign object is given a preliminary classification according to a characteristic of the radiation anomaly caused by the object. The characteristic is a contrast between the a radiation measured at the location of the foreign object and an unmodified radiation emitted by the living tissue without the foreign object According to still further features in the described preferred embodiments the preliminary classification of the foreign object is according to the sign and magnitude of the contrast between the radiation measured at the location of the object and a background radiation level.

According to still further features in the described preferred embodiments, the foreign object is identified based on a spectral scan made at the location of the object. The spectral scan is adapted to the preliminary classification of the object by choosing a frequency band for the spectral analysis, which is optimal to distinguish between at least two objects in the preliminary general category.

According to still further features in the described preferred embodiments, the radiation anomaly is detected in a first frequency band and the spectral analysis is performed in a second frequency band. The second frequency band differs from the first frequency band. To perform the spectral analysis, first, a background signal emanated by the living tissue without the foreign object is measured in the second frequency band. Then the location of the anomaly is scanned in the second frequency band resulting in a second measured signal and a contrast is calculated between the first signal and the second signal.

According to still further features in the described preferred embodiments, spectral analysis is performed on a signal that includes at least one emanation selected from the group consisting of the radiation anomaly resulting from radiation emitted by the living tissue being modified by the foreign object; an output of an external radiation source that interacts with the foreign object; a heat flow from the living tissue; a heat flow from the foreign object.

According to further features in preferred embodiments of the invention described below, the detector identifies the foreign object based on a difference between an unmodified radiation signal from the living tissue without the foreign object and the radiation signal at the location of the foreign object and the difference is quantified as a contrast between the unmodified radiation signal and the second radiation signal at the location of the foreign object.

According to still further features in the described preferred embodiments, the first sensor assembly of the detector of the present invention includes an electronic sensor and the second sensor assembly includes the same electronic sensor and a band pass filter.

According to still further features in the described preferred embodiments, the processing unit of the detector of the present invention is either a human operator or a dedicated electronic processor of a personal computer.

BRIEF DESCRIPTION OF THE DRAWINGS

The invention is herein described, by way of example only, with reference to the accompanying drawings, where.

DESCRIPTION OF THE PREFERRED EMBODIMENTS

The principles and operation of a non-invasive method to identify a hidden foreign object near human skin according to the present invention may be better understood with reference to the drawings and the accompanying description.

It is well known [for example see G. Gaussorgues. La Thermographie Infrarouge. Principes Technologie Applications, Technique et Docum. Lavoisier, Paris, France, 1988, 392 pages; J. M. Lloyd. Thermal Imaging Systems, Plenum, New York, 1975; W. L. Wolfe, and G. J. Zissis, eds., The Infrared Handbook, Environmental Research Institute of Michigan, Ann Arbor, Mich., 1989); V. Kozielkin, I. Usoltzev. The Foundation of Infrared Techniques (in Russian). Moscow, Mashinostroenie, 1985, 264 pages; G. Gryazin. Electro-Optical Systems for Space Looking: The Systems of Television (in Russian). Mashinostroenie, 1988, 224 pages; L. Lazarev. Electro-Optical Systems (in Russian). Mashinostroenie, 1989, 512 pages] that a human body radiates IR radiation as a black body with maximum radiation at about 10 μm which corresponds to medium temperature of the living tissue of a healthy human, 36.5° C.-36.9° C. We present in FIG. 1 the results of measurements of this radiation.

Figure 2:
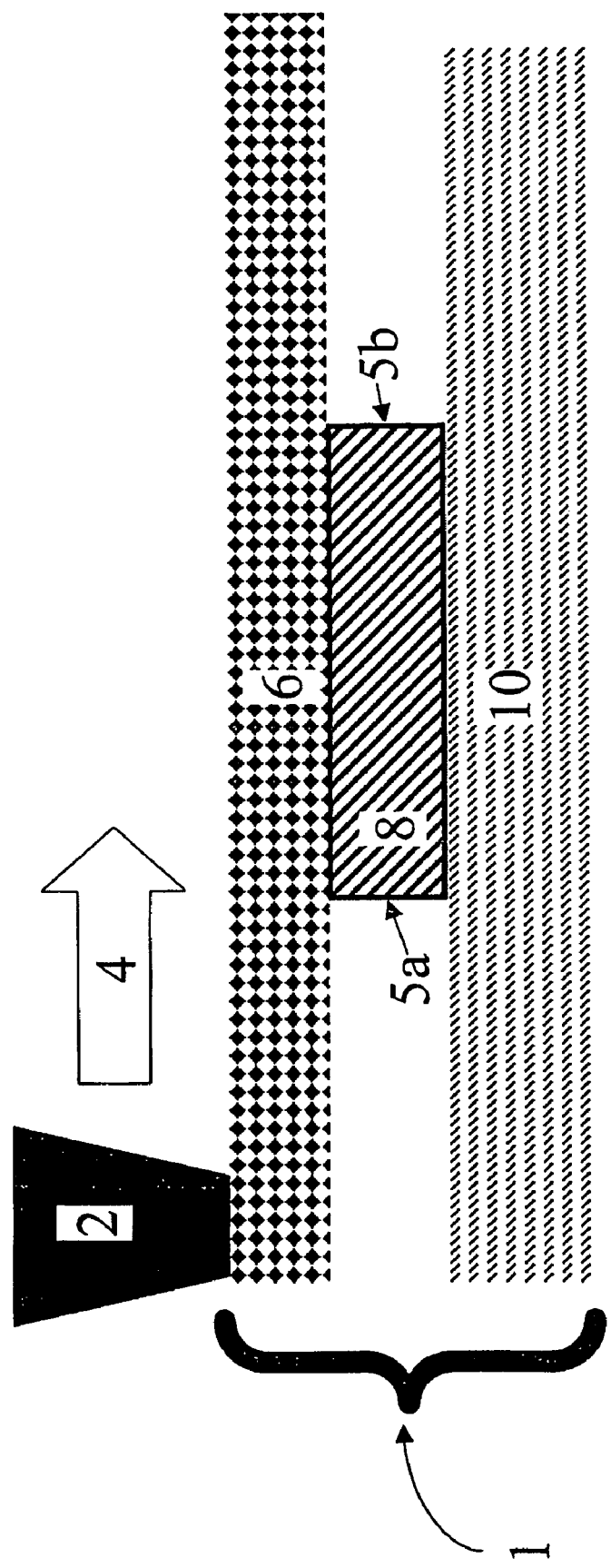
FIG. 2 is a depiction of the physical model that is a basis of the present invention.

A general illustration of the physical model (PM) that is the basis of the present invention is presented in FIG. 2. According to the teachings of the current invention, a foreign object 8 is identified based on interactions between foreign object 8 and infrared radiation emitted by the human body 10. The presence of clothes 6 or foreign object 8 causes changes in the IR radiation field. The nature of these changes in the radiation field is depends on the transparency, reflectance and transmittance of clothes 6 and foreign object 8. In turn, the transparency, reflectance and transmittance of clothes 6 and foreign object 8 are dependent on the substance, geometry and temperature of clothes 6 and foreign object 8. Clothes 6 and foreign object 8 display different transparency, reflectance and transmittance for different wavelengths of the IR radiation band. The intensity of radiation in a given wave band that is emanated by a composite object (as in FIG. 2) wherein a black body heat emitter (human body 10) is obscured by one or more objects (e.g. a foreign object 8, and clothes 6) can be computed using the formulas shown in Table 1 and parameters from Table 2 and Table 3.

The PM of the current invention includes the following basic components (see FIG. 2):

There are three main components: a Radiator, an Object being identified and clothes.

Each component is heated as a planar extended layer with finite thickness. In formula we define:

Radiator—is human body 10, which behaves as a blackbody at temperature $T_R$.

Foreign Object 8—is a selectively emitting body (metal, plastic, etc.) at temperature $T_{FO}$.

Clothes 6—is treated as a gray-body at temperature $T_C$.

The optical parameters that are used in the proposed physical model (PM) are:

Radiator—the spectral density of emitted radiation (dR/dλ) from human body 10 as a black body with temperature $T_R$ (for Radiator), which is assumed to be nearly identical to radiation emitted by an ideal black body heated to the temperature of a human body.

Foreign Object 8—the spectral coefficients of emissivity, $\epsilon(\lambda)$, transparence, $\tau(\lambda)$, and reflectance, $r(\lambda)$ for Foreign object 8; and Clothes 6—integral coefficients of emissivity, $\epsilon$; transparence, $\tau$; and reflectance, r for Clothe 6.

Parameters of the model are presented in Table 2 and Table 3 according to well-known theoretical concept described in the corresponding literature, which are presented in J. D. Lindberg, R. E. Douglass, and D. M. Garvey, "Absorption Coefficient Determination Method for particulate materials", Applied Optics, 1994, vol. 33, No. 19, pp. 4314-4319; G. A. Findlay and D. A. Cutten, "Comparison of the performance on 3-5 and 8-12 µm infrared systems", Applied Optics, 1989, vol. 28, pp. 5029-5037; N. Kolchenogova, B. Uglov, "Radiation transfer through scattering textile materials", Heat Transfer Research, 1993, vol. 25, No. 3, pp. 398-401; T. Jaeger, A. Nordbryhn, and P. A. Stokseth, "Detection of low contrast targets at 5 µm, and 10 µM: a comparison" Applied Optics, 1972, vol. 11, pp. 1833-1835; J. A. Abel, "Radiometrics accuracy of forward looking infrared systems", Optical Engineering, 1977, vol. 16, pp. 241-248; and S. P. Braim, "Technique for the analysis of data from an imaging infrared radiometer", Infrared Physics, 1988, vol. 28, pp 255-261.

Thus from a basic knowledge of the clothes of the subject and using equations from Table 1, a range of normal values of the background radiation level can be computed. Furthermore the expected radiation anomaly due to a foreign object can be determined. Similarly, an unknown object can be identified based on the radiation anomaly caused by the object.

In order to demonstrate the practicality of the above physical model, experiments where conducted and are described in part herein. Integral heat flow from the structures listed in Table 5 in the wavelength range from 3 µm to 40 µm were measured using a pyroelectric detector acquired from ORIEL Instrument Inc, USA. One optical detector was used. The border of an anomaly and the foreign objects' outlines were detected by calculating (counting of gradients of measuring flow) changes in the signal over time while detector moved along a scanning line on the investigated structure surface. In an alternative embodiment, two detectors disposed along the scanning are used and the border of an anomaly is detecting and the outline of a foreign object is defined by measuring the difference between the signals from the two detectors. The calculation of the radiation contrast C was made by use of expression (1A) in Table 1 (Note that in the experiment radiation intensity R' and R" were measured quantities).

Scanning was performed by means of a scanning mirror system. Alternatively scanning is done using a mechanical entrance aperture with changeable entrance hole value or by moving the detector (e.g. investigator waving a hand held detector). The scanning of the investigated structure surface allows marking the outline of the foreign object 8, hidden in the clothes 6 on the human body 10.

According to one embodiment of the current invention, preliminary classification of a foreign object is based on the absolute value of the contrast and the sign of the contrast during the integral scan. For example based on the experimental integral flow measurements, whose data is presented in Table 4 and Table 5, on the overall magnitude (in %) and sign of the contrast for different foreign objects and materials, the first classification of the detected foreign object can be made. Particularly, in the case of summer clothes, positive contrast values of greater than 50% are received only from objects from steel or from objects containing iron, like an electron device having electron elements in a plastic case. Therefore objects producing positive contrast of greater than 70% are identified to have metallic elements of more than 5 mm thickness. Contrast magnitudes of 20% and up to 30% are found for both plastic and explosive materials (e.g. TNT). It is seen in Table 4 that the winter clothes (winter-jacket, hosiery or natural leather, laid and silk-lined) do not always reduce the contrast from a foreign object. Sometimes winter clothes even improve the contrast. The improved contrast occurs for both positive (e.g. electron devices) and negative values of contrast (e.g. plastic). This effect results from the better heat isolation of winter clothes. Increasing the heat isolation increases the absorption of radiation in near IR range (up to 7 µm), and as a result the radiation of far IR range receives the main weight in integral measurement. Thus contrast is increased for those objects whose greatest contrast is in this (far IR) range.

Detailed investigation of 23 different materials (i.e., of different physical models (PM)) is presented in Table 5. It is seen that the magnitude of the contrast is different for different materials and for various clothes (denoted [1-5] in the third column) and contrast is mostly positive. Only for some special kinds of plastics, such as polyester, the sign of the contrast is negative.

Figure 3:
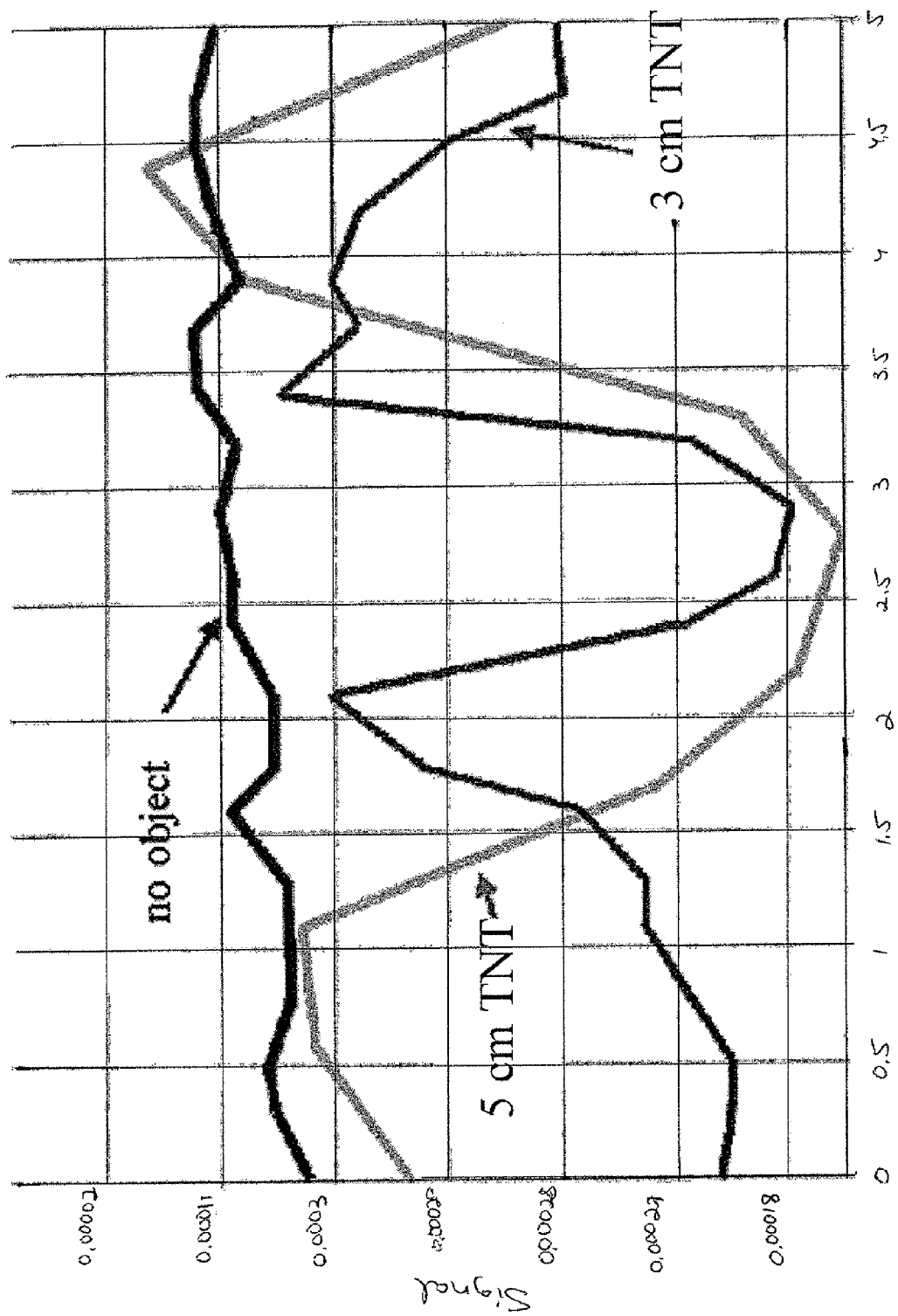
FIG. 3 is a first illustration of the results of an integral scan across the chest of a subject using the methodology of the current invention to detect tablet sized object the subject's shirt pocket.
Figure 4:
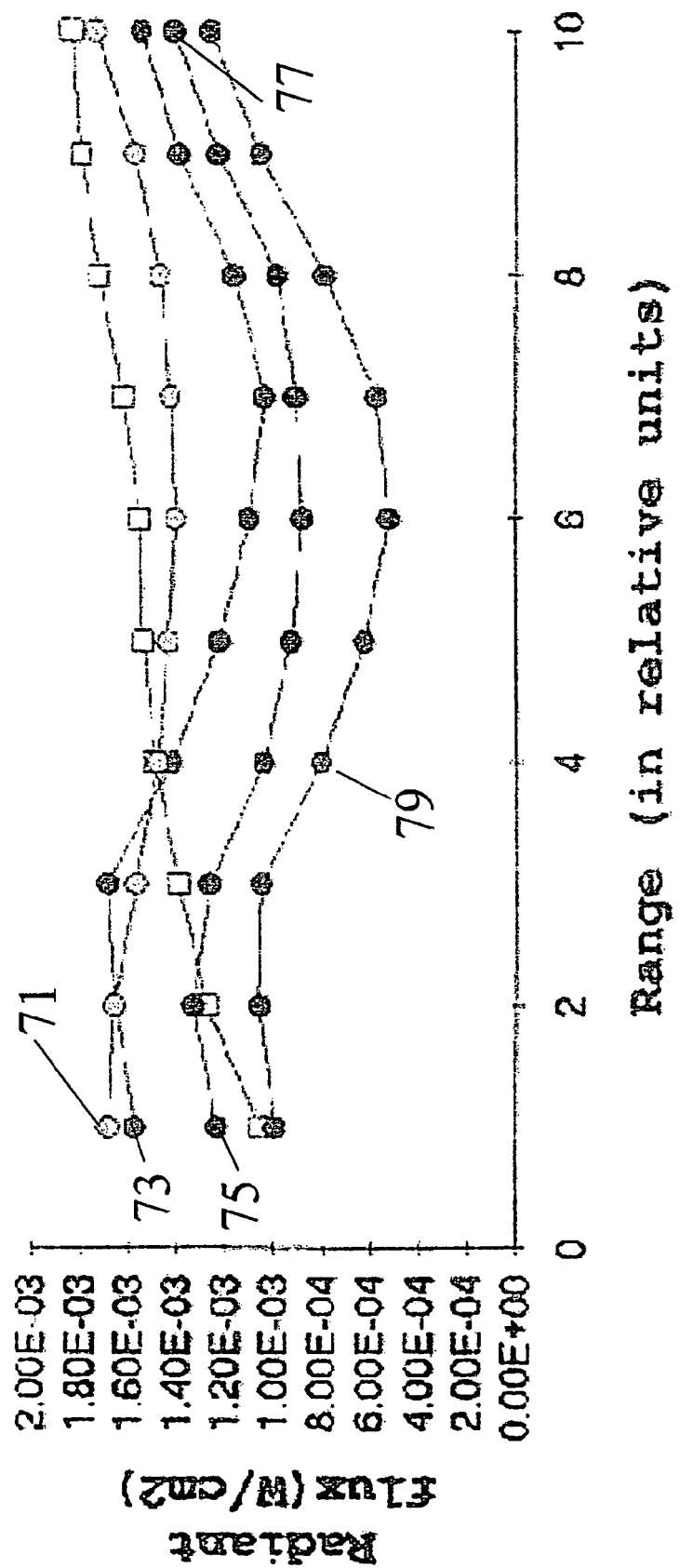
FIG. 4 is a second illustration of the results of an integral scan across the chest of a subject using the methodology of the current invention to detect a tablet sized object in the subject's shirt pocket.

The first preliminary conclusion is that in the integral regime, only explosive materials give stable negative contrast (see Table 5 and also FIG. 3 which shows the integral scan results across the chest of a person having nothing in his pocket, having a 3 cm diameter tablet of TNT in his pocket and having a 5 cm diameter tablet of TNT in his pocket). Some kinds of organic materials (plastics) give both positive and negative contrast. Thus, plastic may give a "masking effect" for identification of explosive materials if only integral regime is used for foreign materials detection and identification. This is illustrated in FIG. 4, showing integral scan results across the chest of a person having nothing in his pocket 71, having a 3 cm diameter tablet of plastic in his pocket 73, having a 5 cm diameter tablet of plastic in his pocket 75, having a 3 cm diameter tablet of TNT in his pocket 77 and having a 5 cm diameter tablet of TNT in his pocket 79 leaves it unclear how one would differentiate TNT from plastic. This difficulty is compounded when the investigator does not know the thickness of the detected object.

Therefore without the spectral regime, it is impossible to identify foreign objects precisely. Investigation of the spectral regime was performed by placing the detector in the zone of the heat flow anomaly found in the integral regime. Measurements of heat flow were then made through the band pass filters of the diffraction type. Particularly band pass filters were acquired from ORIEL Instrument Inc., USA. The diffraction filters for IR the range have pass bands from 100 up to 250 nm. The measurements were made by use one detector through the filters, which were changed in consecutive order.

Figure 5:
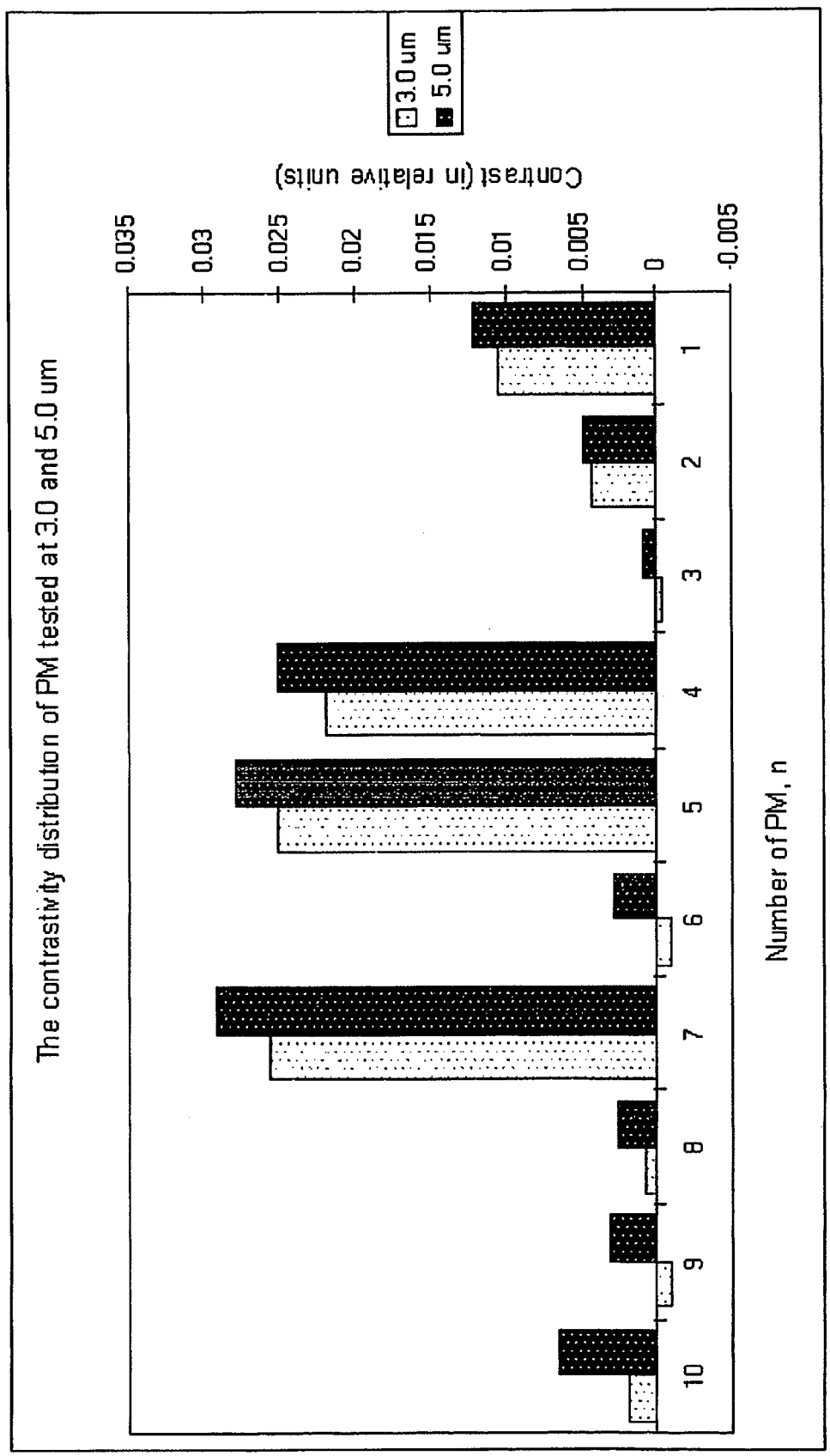
FIG. 5 illustrates distribution of the contrast for the 10 different physical models (PM=combination of clothes and foreign object) listed in Table 6 for $\lambda_1=3$ μm (left columns) and $\lambda_2=5$ μm (right columns)
Figure 6:
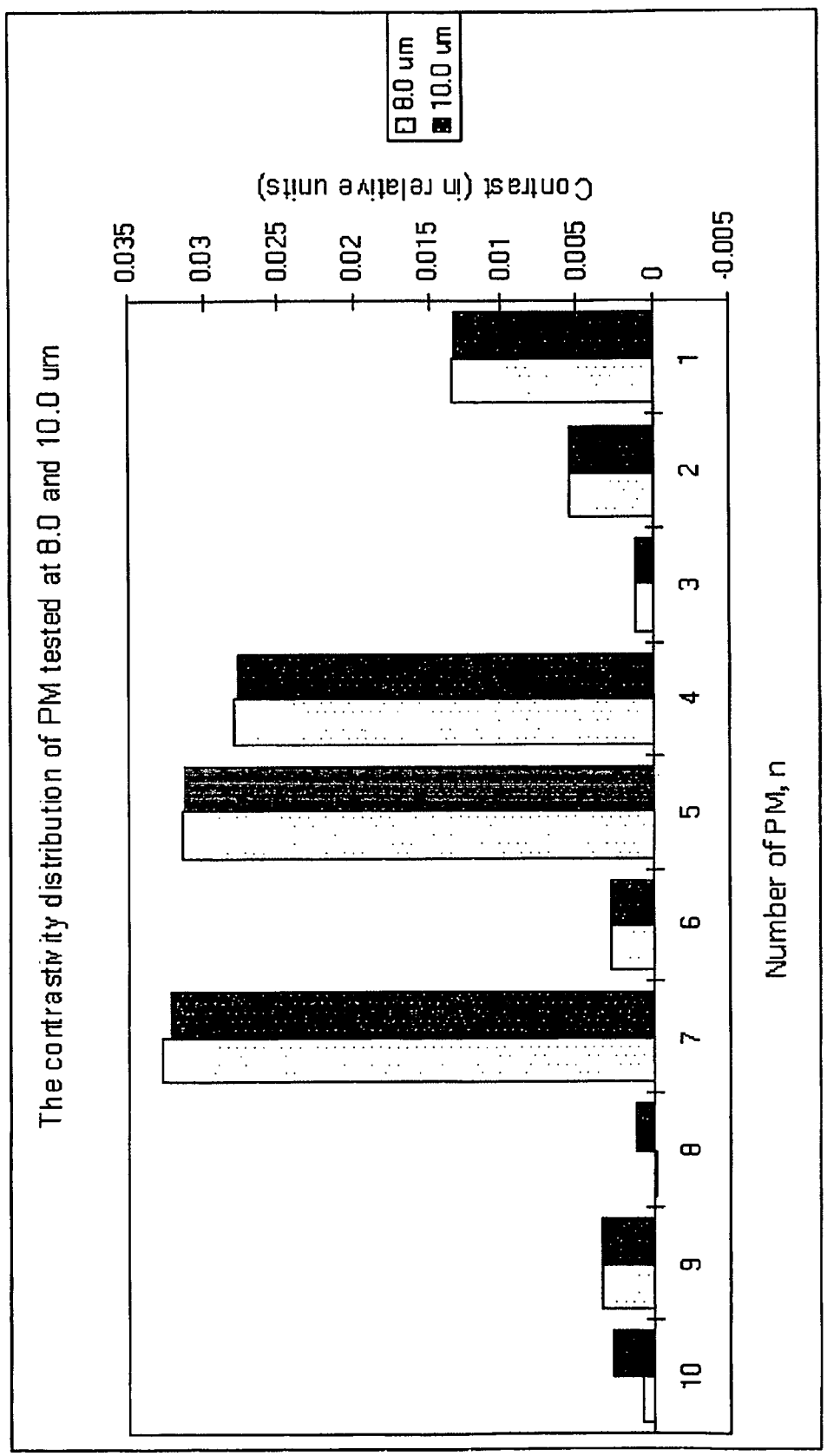
FIG. 6 is the same as FIG. 5, but for $\lambda_1=8$ μm (left columns) and $\lambda_2=10$ μm (right columns)
Figure 7:
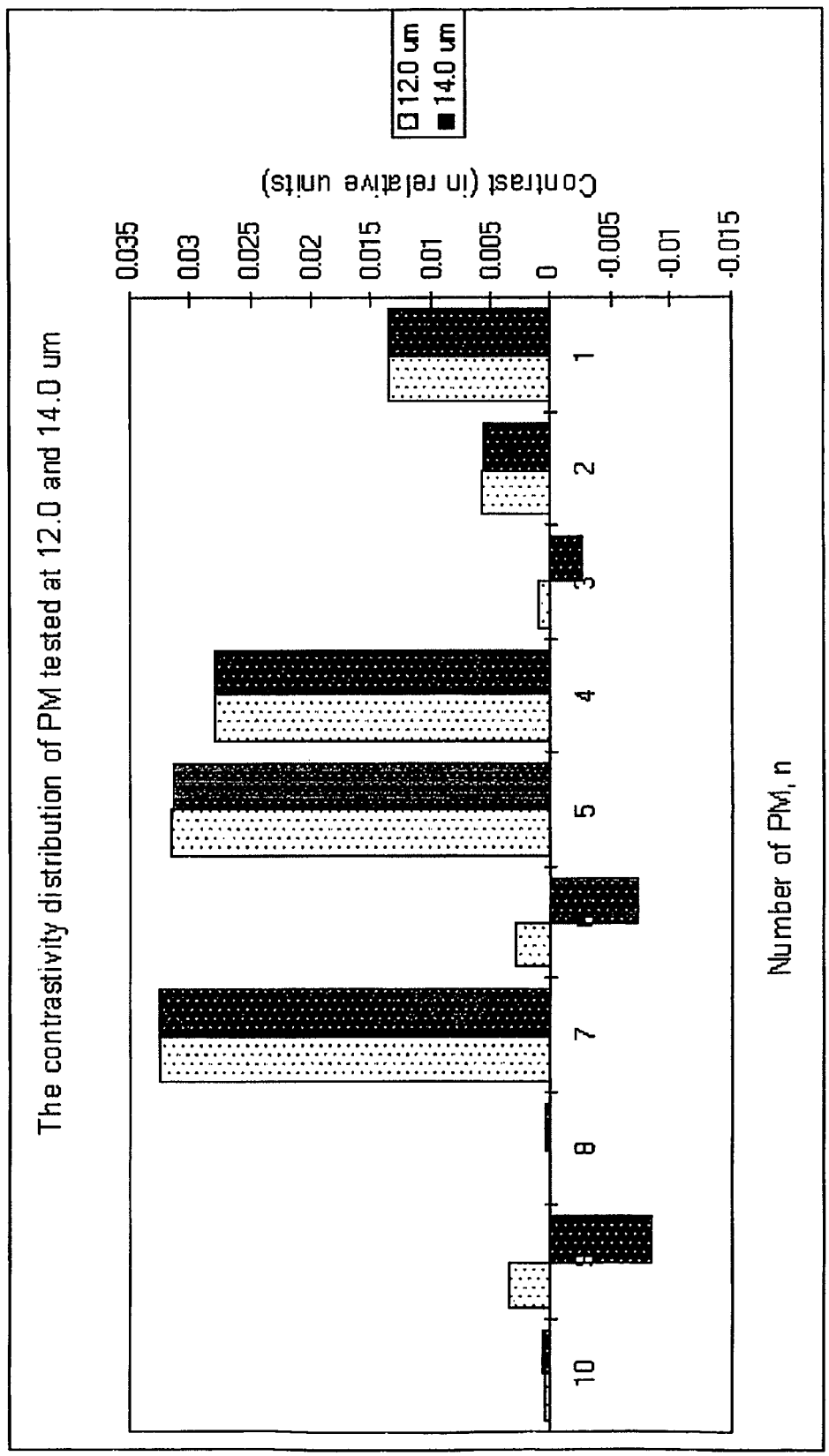
FIG. 7 is the same as FIG. 5, but for $\lambda_1=12$ μm (left columns) and $\lambda_2=14$ μm (right columns)
Figure 8:
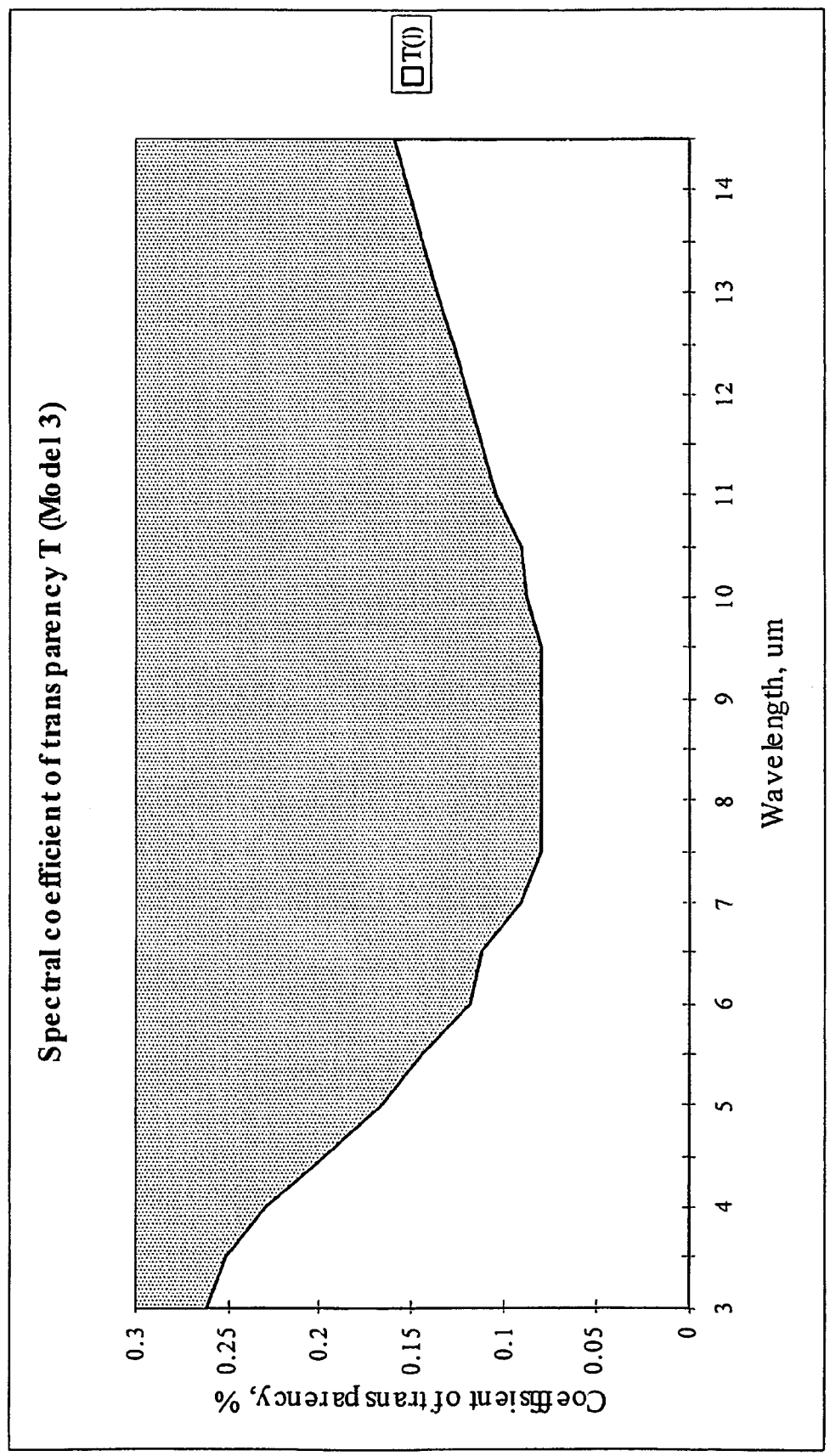
FIG. 8 shows the measured transparency coefficient versus the IR wavelength for PM 3 Table 6.
Figure 9:
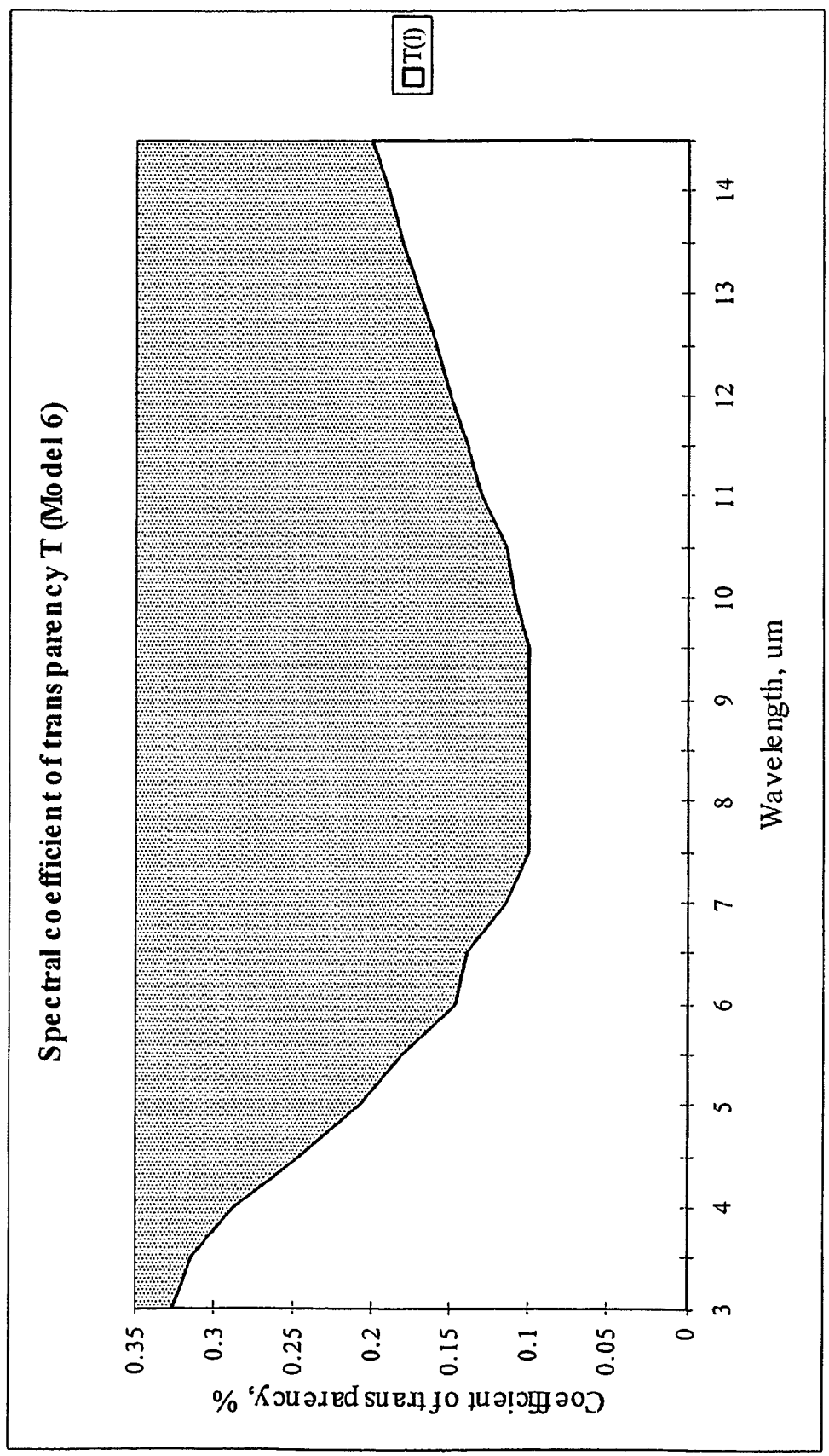
FIG. 9 shows the measured transparency coefficient versus the IR wavelength for PM 6 Table 6.
Figure 10:
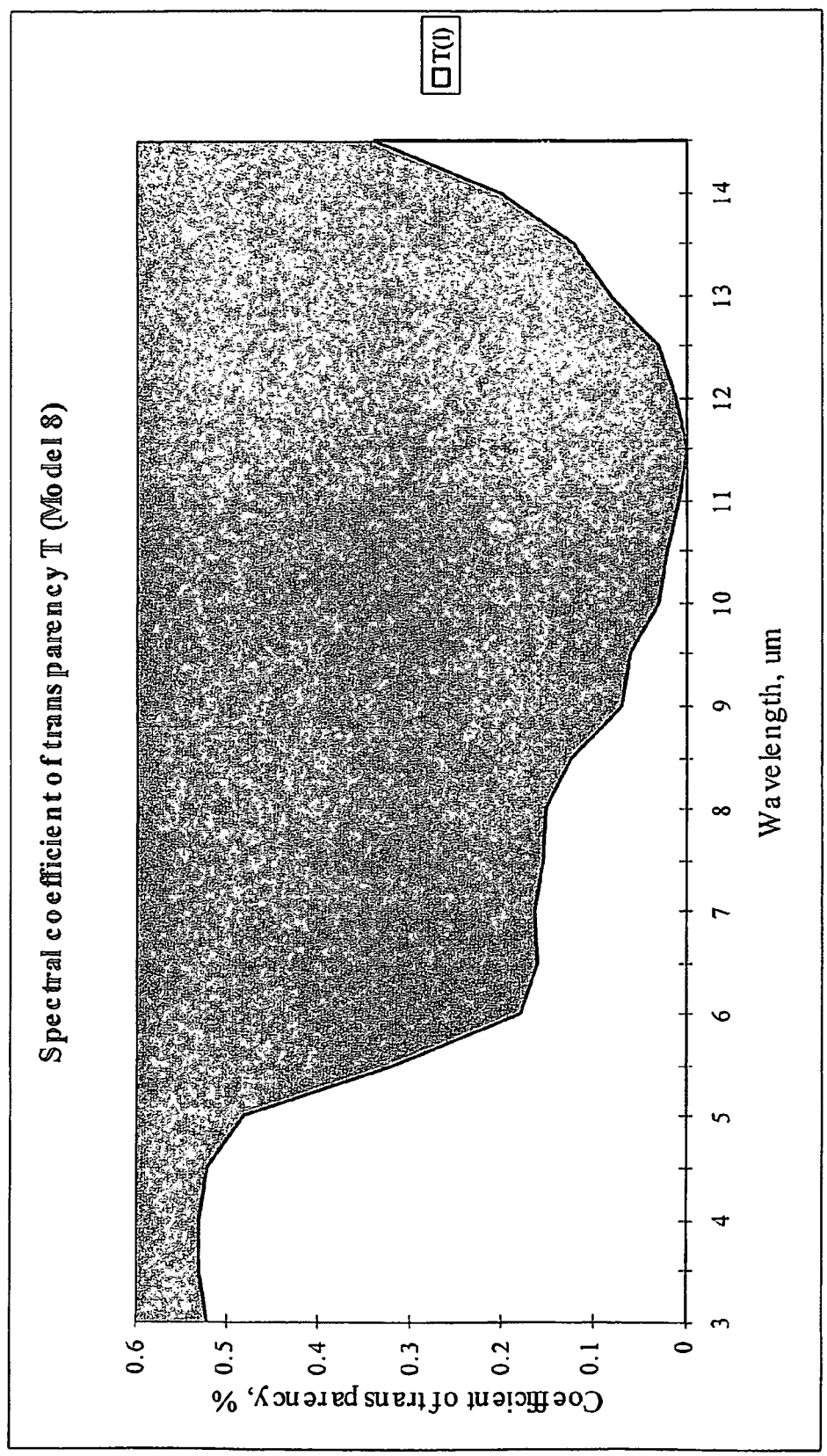
FIG. 10 shows the measured transparency coefficient versus the IR wavelength for PM 8 Table 6.
Figure 11:
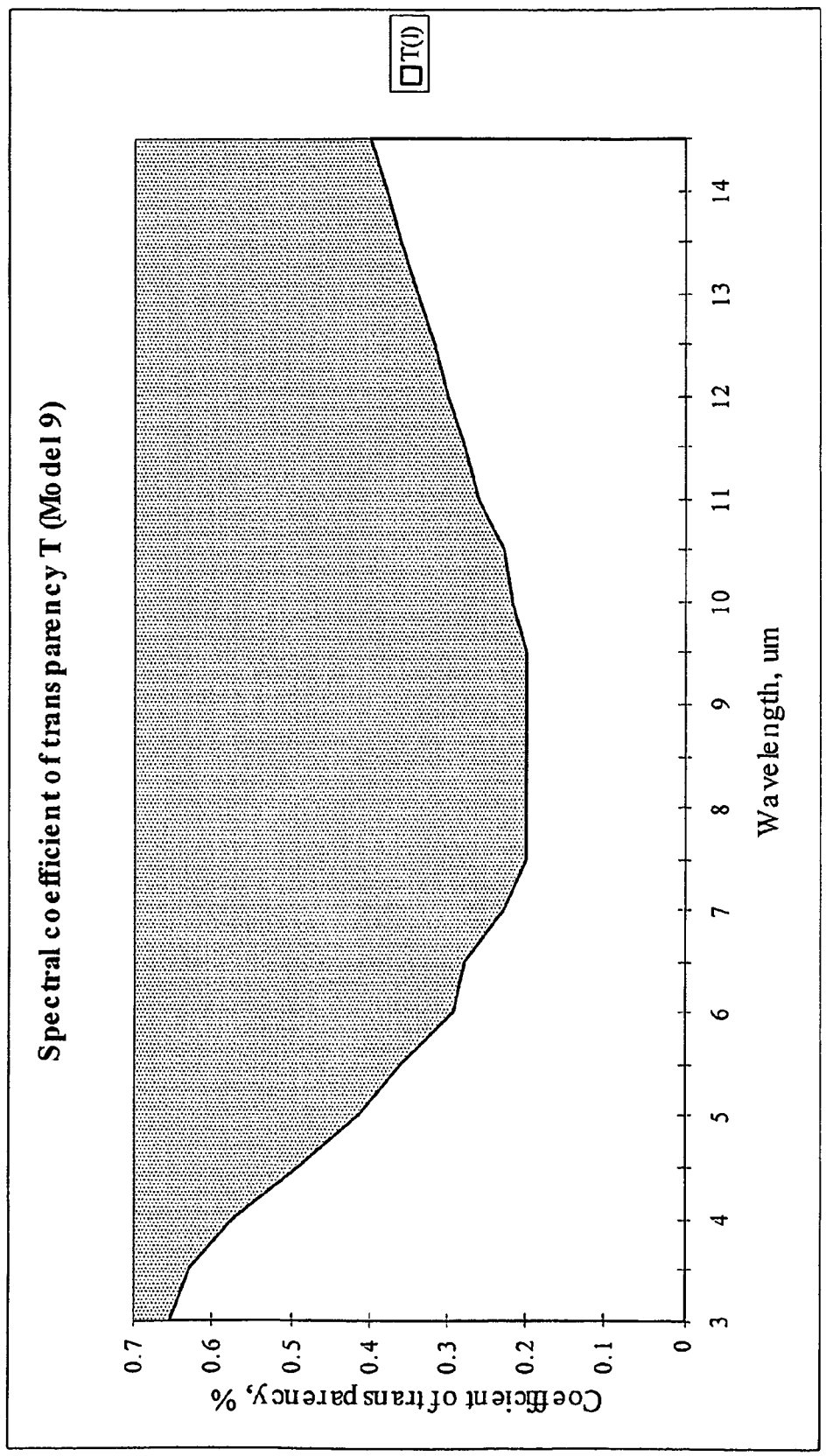
FIG. 11 shows the measured transparency coefficient versus the IR wavelength for PM 9 Table 6.
Figure 12:
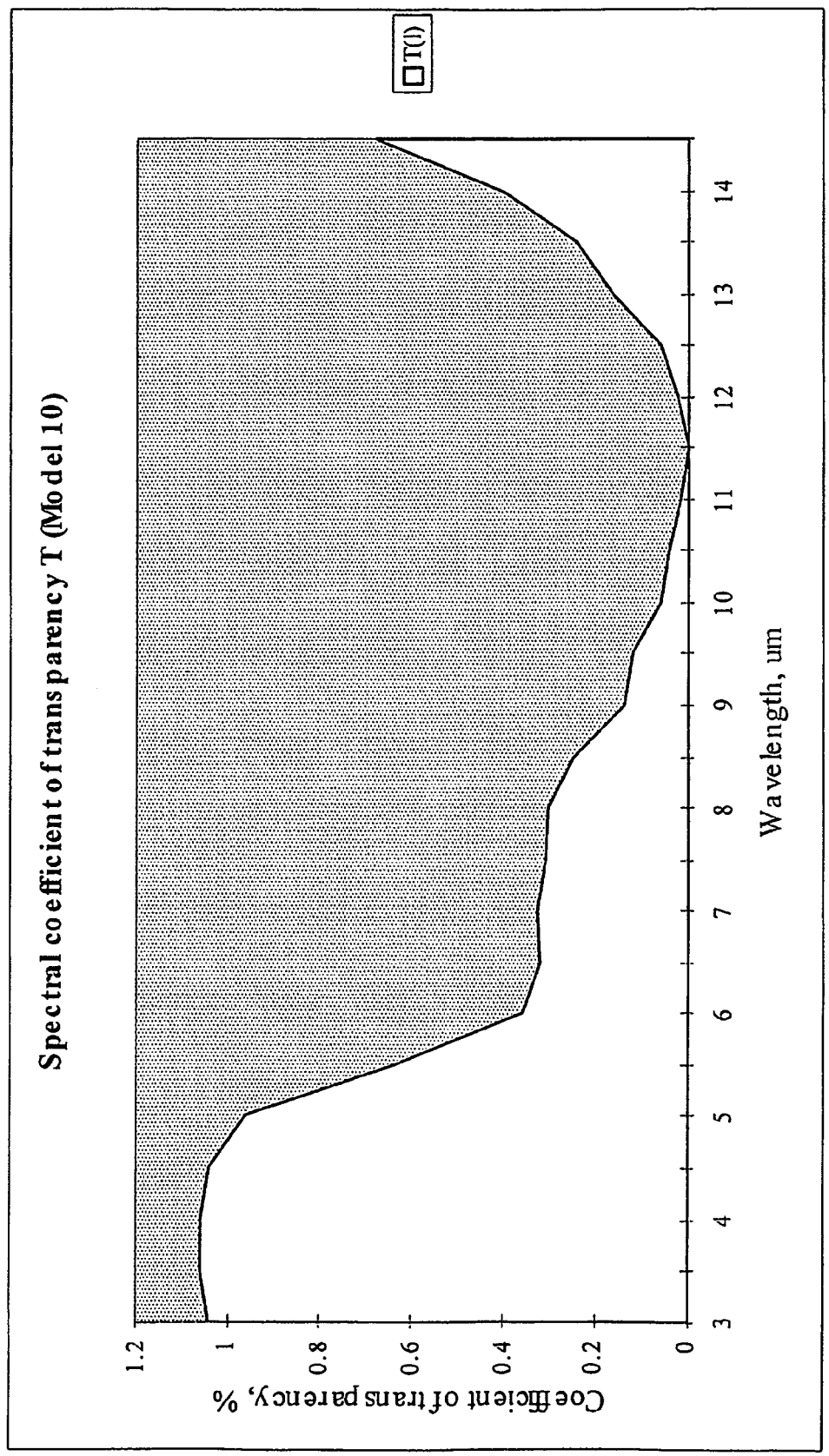
FIG. 12 shows the measured transparency coefficient versus the IR wavelength for PM 10 Table 6.

Investigation of overall contrast magnitude and sign presented in FIG. 5-FIG. 7, which were made for PM 1-10 of Table 6 (denoted by n=1-10 in the corresponding histograms along the horizontal axis, see FIG. 5, FIG. 6, and FIG. 7), have shown that the contrast may significantly change its magnitude and sign depending on the waveband detected by the optical sensor. Therefore, for more complicated physical models (PM of 3, 6, and 8-10 Table 6), transparency was measured experimentally in a spectral mode (see FIG. 8 through FIG. 12). It can be seen that transparency of the foreign objects is very sensitive to the wavelength of observation of the contrast. It is also clear that regardless of the different clothes in PM 3, 6 and 9 the signature of plastic is consistent. Furthermore, regardless of the presence of silk clothing or hosiery, the signature of plastic PM 8 is easily separated from MgO (PM 8 and 10) due to the high transparency of plastic in the bandwidth from 9-13 µm.

The final identification is made according all received results from integral and narrow band passive measurements. This identification is based on choosing the most suitable substances and objects, which have properties similar to those measured. Alternatively, in cases where a more precise identification is needed or where there is a need to detect small quantities of specific materials (for example biological or nuclear materials) the passive IR (integral and spectral regimes may be supplemented by a Geiger counter, a metal detector or an active optical regime (such as irradiating the subject with a low power IR or UV bulb and measuring reflected light).

We refer now to FIG. 2, the physical model of the present invention. A subject 1 (a man passing a security check) is a man wearing clothes 6 and carrying a foreign object 8. The current invention takes advantage of the fact that when the infrared optical field, radiated from body 10 of the subject is influenced by a foreign metallic or dielectric foreign object 8, even if foreign object 8 is hidden or embedded into clothes 6, the difference between the temperature between foreign object 8, human body 10 and the clothes 6 leads to an anomaly in the radiation field emitted by human body 10. A detector 2 detects the anomaly in the radiation field. Detector 2 scans by moving in a direction 4. In FIG. 2, detector 2 has yet to reach foreign object 8. Thus, detector 2 is beyond the boundary of foreign object 8, and detector 2 detects the background radiation emitted by human body 10 and attenuated by interposing clothes 6. As detector 2 scans (moving in direction 4), detector 2 will pass over a leading edge 5a of the foreign object 8. When detector 2 passes leading edge, 5a the detected radiation will jump to the anomalous radiation emitted by human body 10 and attenuated both by clothes 6 and by foreign object 8. As detector 2 continues to scan past trailing edge 5b of foreign object 2 the radiation field jumps again from the anomalous level back to the background level. When detector 2 is located over foreign object 8, the anomaly in the radiation field is detected. When detector 2 is beyond the borders of foreign object 8 (before reaching leading edge 5a or after passing trailing edge 5b) the background radiation field is detected. Thus, after scanning subject 1, the locations of leading edge 5a and trailing edge 5b and therefore the location and geometry in one dimension of foreign object 8 are known. Scanning in various directions and using known tomographic methodologies, the 3-dimensional position of foreign object 8 is measured.

Figure 13:
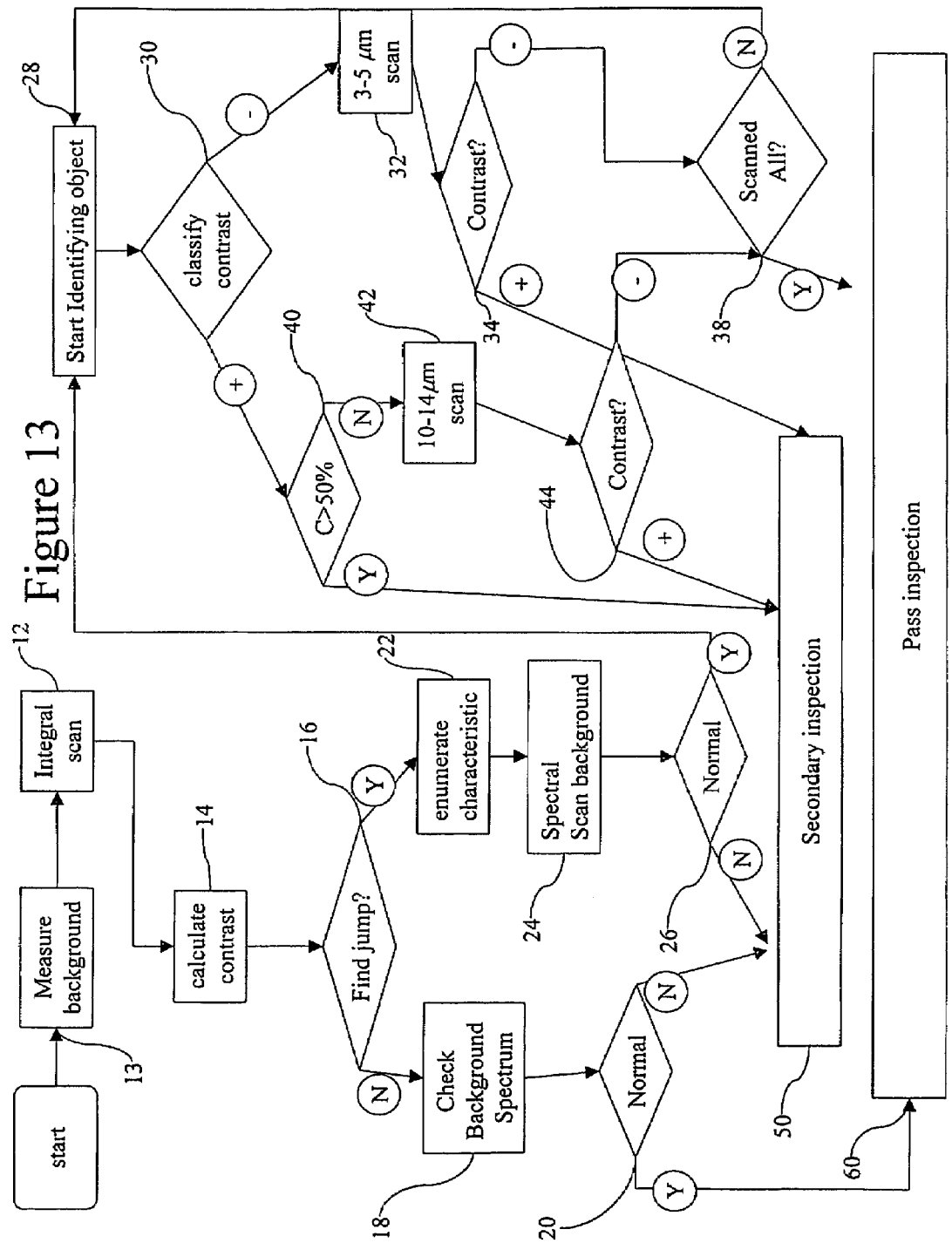
FIG. 13 is a flowchart illustrating a method of identifying a foreign object in the vicinity of a living body according to the current invention.

We refer now to FIG. 13, a flow chart of a first embodiment of the present invention. In FIG. 13 a security guard is using the scanning device of FIG. 14 to test for a foreign objects. First the guard measures 13 the integral background radiation level (unmodified by the presence of foreign object 8).

In the embodiment of FIG. 13, a human operator using a hand held instrument 100 (see FIG. 14) measures 13 an integral background radiation level and calibrates for an integral scan 12 by holding the sensor 108 over a part of subject 1, where there is no hidden object and where the radiation emitted by subject 1 is substantially unmodified by foreign object 8. Sensor 108 is a pyroelectric detector. The pyroelectric detector is sensitive to IR radiation in the bandwidth from 5 µm -20 µm. Thus, integral scan 12 measures the average radiation intensity in this wide bandwidth. To measure 13 the background radiation level and calibrate the instrument, the operator first puts instrument 100 into a integral-background mode by first pressing integral-scan-button 102a and then pressing background-toggle-button 102d. Once in the integral-background mode, the operator starts integral scan 12 by pressing on-button 104e causing instrument 100 to register the mean radiation density (0.0015 W/cm$^2$µm) on gauge 110 and also causing the instrument 100 to calibrates itself by measuring and storing a background radiation level (if there is a foreign object present at this location, the subject will be sent to secondary inspection due to an abnormal background [see step 20 of FIG. 13]).

Figure 1:
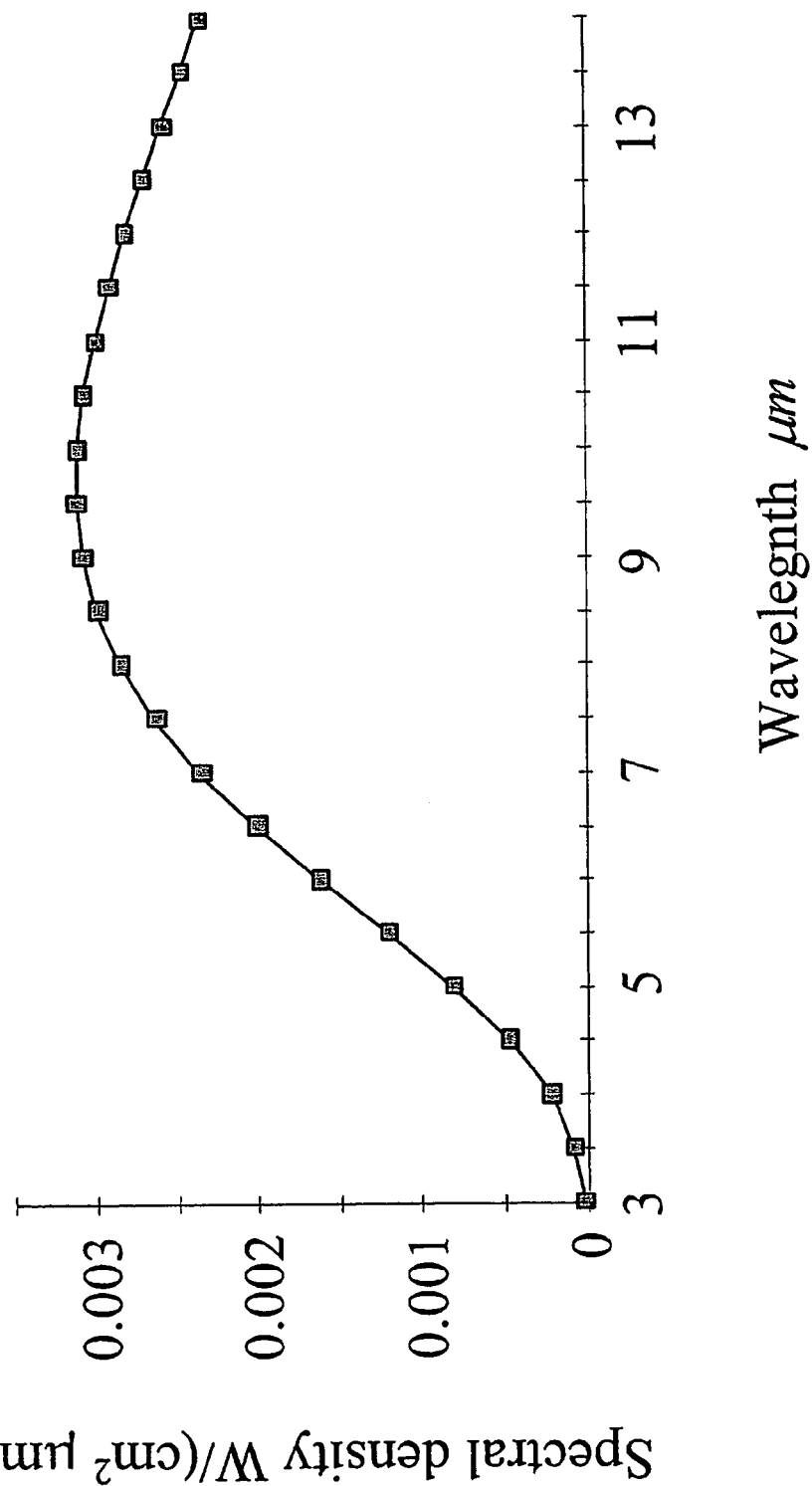
FIG. 1 is an IR spectrograph of radiation emitted by a human body.

Alternatively, an operator measures 13 a background radiation level by calibrating instrument 100 periodically on an airport worker (wearing typical clothes and not having a foreign object), or by manually setting a general expected background radiation intensity level ~2×10$^{-3}$ W/(cm$^2$µm) [See FIG. 1].

Once a background level is set, the operator again presses background-toggle-button 102d to toggle off the background mode and start scanning mode. During the scanning mode, in order to quantify the difference between radiation intensity at the current position and the background radiation intensity, contrast between the current radiation level and the background level is calculated 14 by a microprocessor inside of instrument 100. During scanning mode, contrast is output on gauge 110 rather than the radiation intensity (which is displayed on gauge 110 during the background mode as explained above). Calculation of contrast is illustrated in Table 1 as follows:

A photographic filtering method in visual optics waveband is used, (as described in A. T. Nesmyanovich, V. N. Ivchenko, G. P. Milinevsky, "Television system for observation of artificial aurora in the conjugate region during ARAKS experiments", Space Sci. Instrument, vol. 4, 1978, pp. 251-252. and in N. D. Filipp, V. N. Oraevskii, N. Sh. Blaunshtein, and Yu. Ya. Ruzhin, Evolution of Artificial Plasma Formation in The Earth's Ionosphere, Kishinev: Shtiintsa, 1986, 246 pages, the method has been used previously for identification of artificial plasma formation in the ionospheric plasma and for eliminating effects of clutter and radiation from stars). Following this method, but in applications to infrared (IR) technology, the radiation effects of the foreign objects is quantified using the parameter called the overall heat contrast C see Table 1.

In the first embodiment (instrument 100), the following general steps are performed to detect a foreign object using integral heat contrast:

a) measuring of the space distribution of the integral heat flow radiated from the structure in the range of wavelength from 5 μm-20 μm;

b) detecting and outlining of the anomalies of the heat flow, which we defined above as a contrast, radiated from the structure's surface;

c) classifying the cause of the detected radiation anomaly (the foreign object) by a characteristic of the integral radiation measurement, for example, the sign and the absolute value of the heat flow changes (i.e., the sign and the magnitude of the contrast). Thus, the object is detected and classified according to a preliminary general classification.

When the outer optical field's frequency changes, the contrast of the corresponding foreign structure is also changed, and the resulting contrast can be positive or negative at the optical recorder. The operator finds 16 an anomaly in the radiation field by noticing any jump in the contrast representing the border of foreign object 8. The detection of metallic or dielectric foreign object 8 is made according the level of the resulting contrast. This integral method provides a reliable definition of the location and dimensions of the detected foreign object, because the interaction of the infrared field irradiated from human body 10, as a passive source of infrared radiation with the foreign object is going on not only near the contour of foreign object 8, but at the some distance from it. Unlike previous art methods and devices, the current invention uses a wide range of frequencies in the integral regime. Thus, the current invention can detect a wide array of objects hidden behind clothing and even under human skin.

In scanning mode, the operator holds down on-button 104e while passing instrument 100 along human body 10 of subject 1. Gauge 110 registers the magnitude of contrast between the measured radiation at the current focus of sensor 108 and the measurement of background radiation stored during the calibration step. When the absolute value of the contrast is greater than a threshold (2%), an alarm is sounded over loudspeaker 105 to alert the operator that the current location contains a radiation anomaly. The operator enumerates 22 characteristics of the radiation anomaly including the location of the wand when there the jump in contrast occurs and in the contrast at the location of the anomaly in the radiation field.

Figure 14:
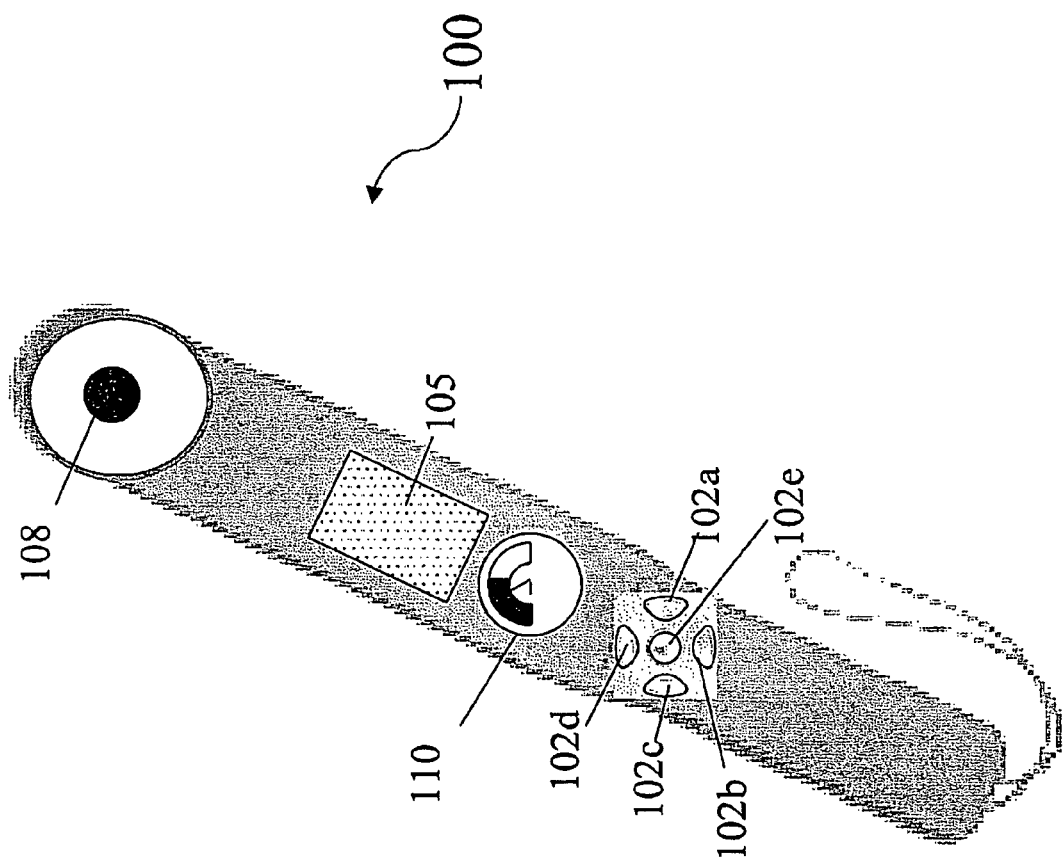
FIG. 14 is a drawing of a first embodiment of the current invention, the embodiment being a handheld device having a single pyroelectric sensor.

If the operator finds 16 no jumps in the measured radiation during the integral scan 12 and then there are no locations of radiation anomalies that need to be scanned. Nevertheless, the operator checks 18 that the background radiation is normal not only in its integral value, but also in narrow spectral bands. The instrument of FIG. 14 is capable of measuring three narrow bandwidth portions of the spectrum. The first narrow bandwidth is 5-7 μm. To check 18 a background radiation level in this bandwidth, the operator first depressing button 102b to set the 5-7 μm band pass filter. Then in order to make a background scan the operator first toggles-on the calibration function by depressing background-toggle-button 102d, and starts measuring the background radiation level by depressing the on-button 102e. Similarly to check 18 a narrow bandwidth spectral measurement at 10-14 μm, button 102c is pressed. Then in order to make a measurement, the background toggle button 102d is depressed, and finally to actually start measuring the background radiation, on-button 102e is depressed. Then the background radiation level registered as a radiation intensity on gauge 110. If the intensity of all of the narrow band measurements is determined 20 to be within a range considered normal, subject 1 passes inspection 60 and is allowed to continue to his destination in the security zone. If one measured background radiation level is not within a normal range, subject 1 is sent to secondary inspection 50.

When the operator finds 16 jumps in contrast during integral scan 12, then the operator enumerates 22 the characteristics of the jumps (locations and measured contrast) for each foreign object. The operator then chooses a location where no foreign object was detected and for each spectral band first performs 24 a spectral background measurement (as described above step 18). The result is the spectral background level (i.e. a background energy level for each wavelength $[R''(\lambda)]$. If a background radiation level in the spectral measurement is determined 26 to be not within a range considered normal, the subject is immediately sent to secondary inspection 50.

If a background radiation level and the results of the spectral measurement is determined 26 to be within a range considered normal 24, then a location of an unidentified object is chosen and the operator identifies 28 the object. Particularly, the operator first preliminarily classifies 30 foreign object 8 according to characteristics of the contrast of the integral measurement. If the contrast is positive and it is greater than 50% 40, then the object is classified as a metal object (according to Table 5 only metal objects have such high positive contrast) and the subject is sent to secondary inspection 50. If there is a positive contrast 30 of less then 50% 40, then the object is classified as either metal, polyester or polyethylene (according to Table 5 all of these substances display high positive contrast). Therefore, the spectral scan is adapted to differentiate between metal and polyester and polyethylene by choosing a narrow spectral band 10-14 μm. The 10-14 μm band is optimal for differentiating these materials because in this band metal displays a positive contrast while plastics display negative contrast as can be seen in FIG. 7. After calibrating the scanner at 10-14 μm by evaluating the radiation intensity in this band at a background location (as described above in step 18) the background-toggle-button is depressed (toggling off the background mode) and the location of the object is scanned 42 at 10-14 μm by holding the sensor over the location of the detected object and depressing on-button 102e. If the contrast is determined 44 to be positive in 10-14 μm scan 42, then foreign object 8 is identified as metal and subject 1 is sent to secondary inspection. If the contrast is determined 44 to be negative in 10-14 μm scan 42, then object 8 is identified as plastic and non-threatening. If there are found 38 more unidentified objects, then identification starts 28 for the next unidentified object. If there are not found 38 any more unidentified objects, then subject 1 passes inspection 60.

If the characteristic of the integral scan of the location of object currently being identified is a negative contrast, then the object is preliminarily classified 30 as either plastic or an explosive. The spectral scan is adapted to differentiate between plastic and an explosive by choosing a narrow spectral band of 5-7 μm. The 5-7 μm band is optimal for separating explosives from plastic because at 5-7 μm, plastic has a positive contrast (as shown for objects 3, 6, and 9 in FIG. 5) and explosives have a negative contrast. The location is then scanned 32 in the spectral mode at the 5-7 μm wavelength band. If the contrast of 5-7 μm scan 32 is determined 34 to be negative, then subject 1 is identified as suspected of holding a hidden explosive device and is sent to a shielded room for special inspection. If the contrast of 5-7 μm scan 32 is determined 34 to be positive, then the object of the current location is identified as plastic and if there are not found 38 any other unidentified object, then subject 1 passes inspection 60 and is allowed to go on to his intended destination.

Figure 15:
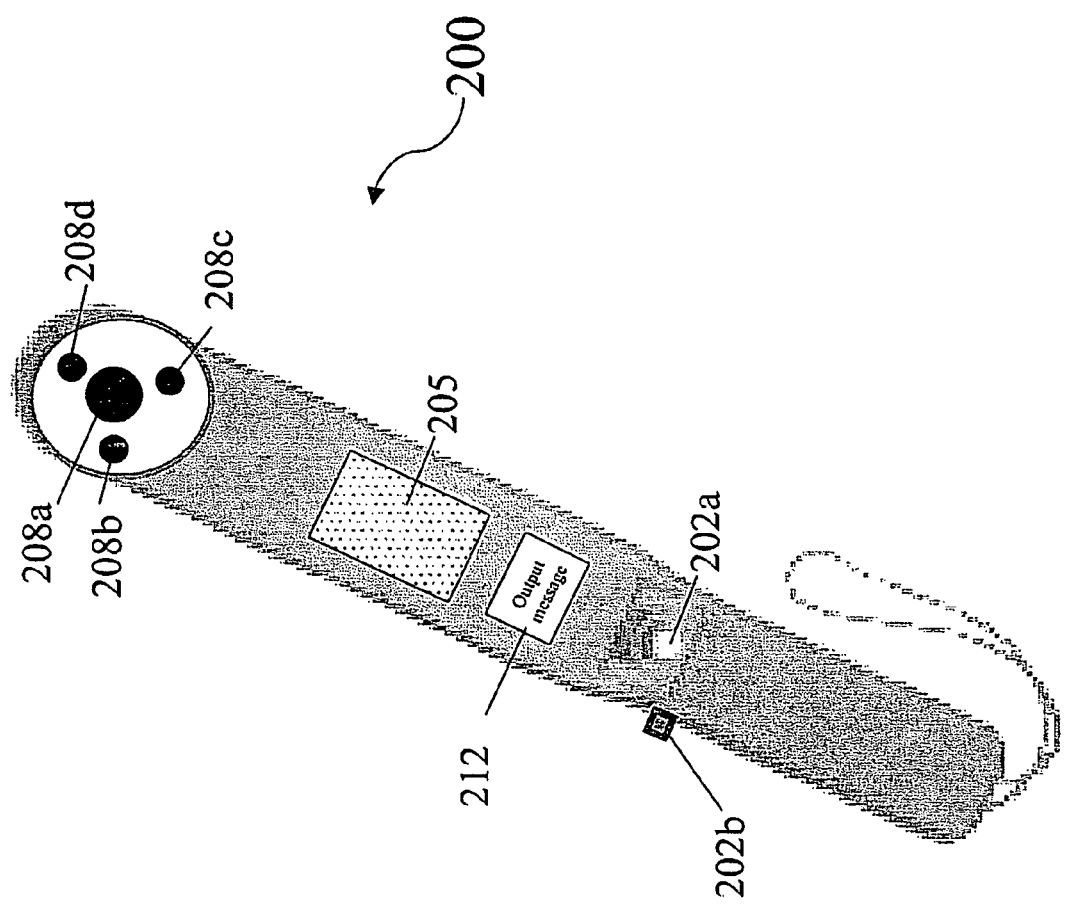
FIG. 15 is a drawing of a second embodiment of the invention, the embodiment being a handheld device having a multiple pyroelectric sensors.

We now refer to FIG. 15, a second embodiment of the current invention. The embodiment of FIG. 15 includes multiple sensors assemblies 208a, 208b, 208c, and 208d. Each sensor assembly 208a-208d, is configured to perceive radiation in a different bandwidth. Particularly, sensor assembly 208a is configured to be sensitive to radiation in a wide spectrum from 5 μm-20 μm; sensor assembly 208b is configured to be sensitive to radiation from 4.5 μm-5.5 μm; sensor assembly 208c is configured to be sensitive to radiation from 13.5 μm-14.5 μm; and sensor assembly 208d is configured to be sensitive to radiation from 9.5 μm-10.5 μm.

The embodiment of FIG. 15 of an instrument 200 is supplied with two buttons, and on-button 202a and a background-calibration-button 202b. When on-button 202a and background-calibration-button 202b are depressed simultaneously, instrument 200 measures and detects a background radiation level simultaneously with all four sensor assemblies 208a-208d and stores a background level for each of the four corresponding bandwidths. If the background level in one of the bandwidths is outside of a preset "normal" range, the instrument notifies the operator by sounding an alarm on loudspeaker 105 and displays a message explaining the nature of the abnormal reading (high or low radiation levels in a particular bandwidth) on LCD display 212.

When only on-button 202a is depressed, instrument 200 detects radiation levels using all four sensors 208a-208d each measuring radiation in a corresponding bandwidth. A microprocessor inside of instrument 200 compares the measured radiation level in each bandwidth with the radiation level of the corresponding bandwidth stored during the background-calibration step. Results are displayed on LCD display 112. When a foreign object 8 causes a jump in the contrast of at least one of the bandwidths beyond a threshold value (absolute value of 2%) then the operator is notified by an alarm over speaker 205. Thus, the integral mode of scanning simultaneously detects anomalies in the radiation signal in all four bandwidths. This increases the sensitivity of instrument 200, because while it is conceivable that heat variations would mask the presence of an object on one particular wave band, it is almost certain, that any object will produce an anomaly in radiation in at least one of the four bandwidths.

Simultaneously, when an object is detected, LCD screen 112 presents a message identifying the object. Specifically, identification is based on analysis by the microprocessor of the contrast in the four bandwidths. For example, if all four sensors assemblies (208a-208d) detect a positive contrast, the LCD displays the message "metal object detected). If all four sensors assemblies (208a-208d) detect a negative contrast, the LCD displays the message "explosives detected." Alternatively, when explosives are detected, the, loudspeaker 105 is deactivated in order to allow evacuation of the area before alerting subject 1 that explosives have been detected. If sensor assembly 208d senses a negative contrast while some of the remaining sensors 208a-208c register a positive contrast, LCD display 212 displays a message "Plastic object detected".

Figure 16:
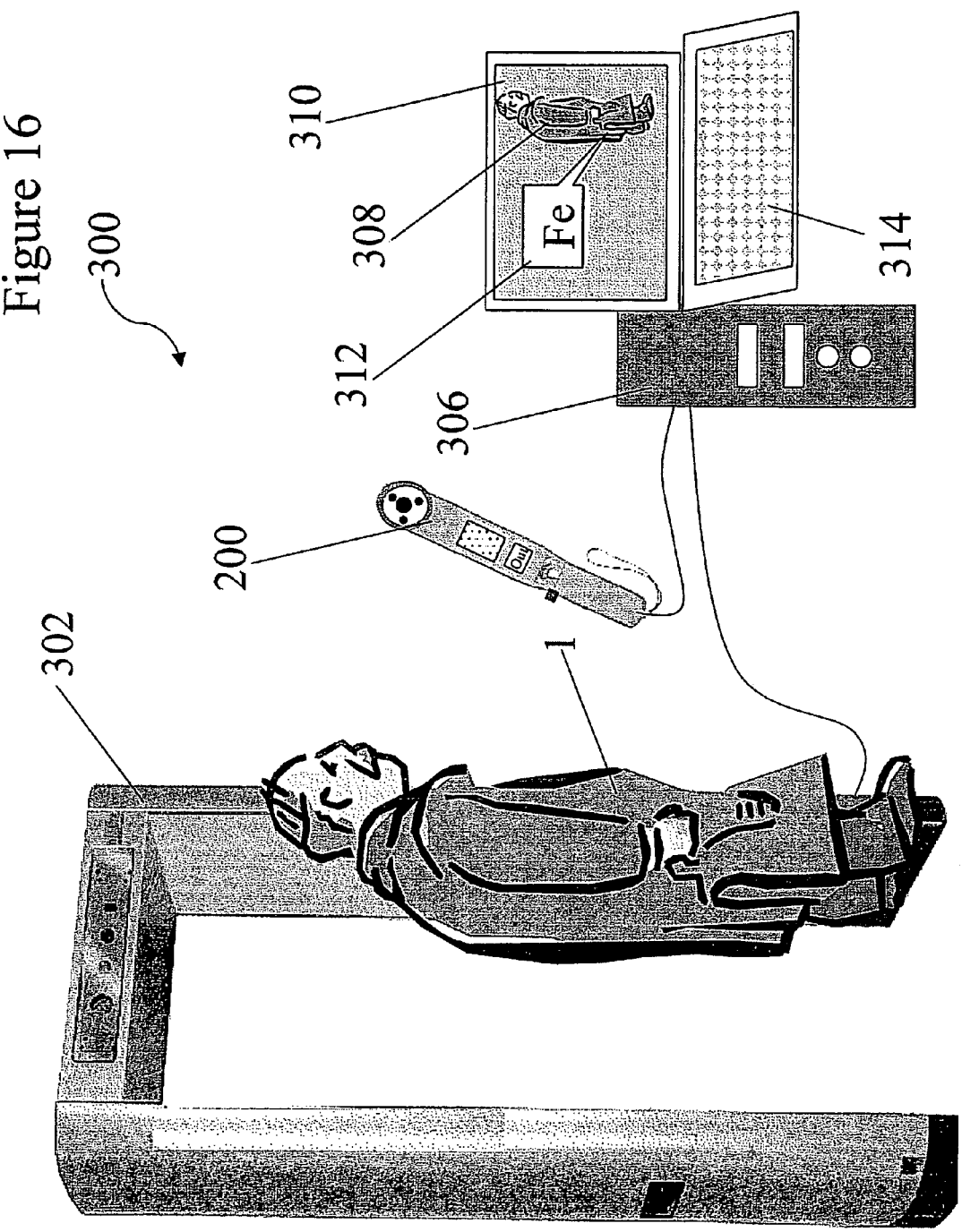
FIG. 16 is a drawing of a third embodiment of the invention, the embodiment including a full body scanner with computer controlled graphical interface.

FIG. 16 illustrates a third embodiment of an instrument 300 to detect and identify foreign object 8 according to the present invention. A fill body scanner 302 contains sensors configured to scan across a subject 1. Full body scanner 302 may be a simple metal detector, or it may include more sophisticated sensors. If fast conclusive results are important and money is not an object, full body scanner may contain multiple IR sensor assemblies. Full body scan results are sent to a desktop computer 306. Desktop computer 306 conveys an image 308 of subject 1 to a display device 310 (a computer monitor). Also output to the display device 310 is a label 312, showing the state of identification of foreign objects in the vicinity of subject 304. For objects that are not yet fully identified, the operator has a hand scanner instrument 200, which is also integrated to desktop computer 306. Thus, when the operator scans an unidentified object with instrument 200, the output of instrument 200 is registered by desktop computer 306. Furthermore, computer 306 includes 3D tomography software that tracks the location of instrument 200. Thus information from scanner 200 is automatically added to a database on subject 1 and based on the location and results of the scan, unidentified object label 312 is updated according to the results of a scan using instrument 200. Alternatively, rather than then automatically tracking the location of instrument 200, the operator clicks with a pointer device on label 312 informing desktop computer 306 that the results of the last scan of instrument 200 apply to the object marked by label 312 and desktop computer 306 automatically updates the database and display.

It is understood that scanner assembly 302 facilitates fast recognition of a large number of foreign objects by an operator. Furthermore, the operator of scanner assembly 302 is located at a distance from subject 1 and therefore is safe from attack or explosions initiated by subject 1. Scanner assembly 302 is further controlled via desktop computer 306. Thus the operator can adjust contrast, image quality, scanning speed, and scanning frequency bandwidth using a keyboard 314. Alternatively, scanner assembly 302 is also equipped with special detectors for example a metal detector, a Geiger counter and an active scanner in the optical or ultraviolet bandwidth to further facilitate positive identification particular substances in smaller quantities than those detectable by IR scanning.

It will be appreciated that the above descriptions are intended only to serve as examples, and that many other embodiments are possible within the spirit and the scope of the present invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Tables

TABLE 1

Formula for calculating the contrast - A formula for calculating contrast between radiation flux measured from a human body in the presence a foreign object and radiation flux from a human body in the absence of a foreign object.

| | |
|---|---|
| $C(\delta\lambda) = [R_c''(\delta\lambda) - R_c'(\delta\lambda)]/[R_c''(\delta\lambda) + R_c'(\delta\lambda)];$ | (1A) |
| $R_c'(\delta\lambda) = R(\delta\lambda)\delta\lambda\{[\epsilon_S(\delta\lambda)\tau_O(\delta\lambda) + \epsilon_O(\delta\lambda)]\tau_C(\delta\lambda) + \epsilon_C(\delta\lambda)\};$ | (1B) |
| $R_c''(\delta\lambda) = R(\delta\lambda)\delta\lambda[\epsilon_S(\delta\lambda)\tau_C(\delta\lambda) + \epsilon_C(\delta\lambda)\};$ | (1C) |
| $R'(\delta\lambda) = \Sigma\{R\lambda_{\xi}\} = \Sigma C_1\lambda_{\xi}^{-5}[\exp(C_2/\lambda_{\xi}T) - 1]^{-1};$ | (1D) |
| $C_1 = 3.74\ 10^{-16}\ Wm^2;\ C_2 = 1.44\ 10^{-2}\ mK;$ | (1E) |
| $\epsilon_C(\delta\lambda) = \epsilon;\ \tau_C(\delta\lambda) = \tau;$ | (1F) |
| $T(\delta\lambda) = [\tau_O(\delta\lambda)\ \tau_C(\delta\lambda)]100\%.$ | (1G) | where:

$R'_c(\delta\lambda)$ is an emitted radiation flux from the Human Body, when the Foreign Object (FO) (as a component of PM) presents;

$R'_c(\delta\lambda)$ is an emitted radiation flux from Human Body, when the FO (as a component of PM) is absent;

$R'(\delta\lambda)$ is an emitted radiation flux from black-body (human skin) in spectral step $\delta\lambda$ at temperature $T_R$;

$\delta\lambda$ is $(\lambda max-\lambda min)/N$; $\lambda min<\lambda_\xi<\lambda max$;

N is a number of steps in spectral range $\Delta\lambda=(\lambda max-\lambda min)$;

$C(\delta\lambda)$ is a contrast in spectral step $\delta\lambda$;

$T(\delta\lambda)$ is a spectral coefficient of optical transparence of emitted radiation from black-body, through the Object and Clothes, at temperature T in spectral step $\delta\lambda$. This coefficient (in %) determines the share of radiation penetrated (run) through the PM components;

$\epsilon_s$ is the heat radiation coefficient of blackness of the human skin;

$\epsilon_o$ is the heat radiation coefficient of blackness of the foreign object;

$\epsilon_c$ is the heat radiation coefficient of blackness of the clothes;

$\tau_o$ is the transparent coefficient of the foreign object;

$\tau_c$ is the transparent coefficient of the clothes.

TABLE 2

Optical properties of the clothes - The optical properties of clothes used in equations predicting the integral heat flux.

| No. | Name of the Clothe | | The values of coefficients | | |
|---|---|---|---|---|---|
| | | | $\epsilon$ | $\tau$ | $\rho$ |
| 1 | Hosiery: | Yellow | 0.720 | 0.010 | 0.270 |
| | | blue | 0.840 | 0.005 | 0.155 |
| | | red | 0.760 | 0.008 | 0.232 |
| 2 | Flax | | 0.340 | 0.010 | 0.650 |
| 3 | Silk (cream) | | 0.580 | 0.002 | 0.580 |

TABLE 4

Seasonal investigations of the contrast - The overall contrast for common foreign objects in the presence of winter and summer clothing.

| | Contrast of the heat flow anomaly | | | |
|---|---|---|---|---|
| | | Magnitude of contrast (in %) | | |
| Season | Sign of contrast | from | up to | Type of foreign object |
| Summer | + | 55% | 75% | Steel, |
| Winter | + | 45% | 70% | thickness 0.3-5 mm |
| Summer | + | 35% | 70% | Electron device in plastic case |
| Winter | + | 35% | 80% | total thickness 40-50 mm |
| Summer | − | 20% | 30% | Explosive materials (like TNT) thickness about 20 mm |
| Summer | +, − | −10% | +30% | Plastic (PVC, Polyethylene, Polyester) |
| Winter | +, − | −25% | +10% | thickness 0.5-5.4 mm |
| Summer | + | 10% | 20% | Black rubber, including porous, thickness 2-3 mm |

TABLE 3

Optical properties of the common substances - The optical properties of common substances used in equations predicting the integral heat flux in the presence of a foreign object.

| $\lambda$ | Aluminum | | | Iron | | | Plastic | | | Magnesium oxide | | |
|---|---|---|---|---|---|---|---|---|---|---|---|---|
| $\mu m$ | $\epsilon(\lambda)$ | $\tau(\lambda)$ | $\rho(\lambda)$ | $\epsilon(\lambda)$ | $\tau(\lambda)$ | $\rho(\lambda)$ | $\epsilon(\lambda)$ | $\tau(\lambda)$ | $\rho(\lambda)$ | $\epsilon(\lambda)$ | $\tau(\lambda)$ | $\rho(\lambda)$ |
| 3 | 0.12 | 0 | 0.88 | 0.16 | 0 | 0.84 | 0.57 | 0.32 | 0.1 | 0.28 | 0.52 | 0.2 |
| 3.5 | 0.1 | 0 | 0.9 | 0.14 | 0 | 0.86 | 0.59 | 0.31 | 0 | 0.29 | 0.53 | 0.18 |
| 4 | 0.08 | 0 | 0.82 | 0.12 | 0 | 0.88 | 0.61 | 0.28 | 0.1 | 0.31 | 0.53 | 0.16 |
| 4.5 | 0.08 | 0 | 0.91 | 0.1 | 0 | 0.9 | 0.65 | 0.24 | 0.1 | 0.33 | 0.52 | 0.15 |
| 5 | 0.07 | 0 | 0.93 | 0.09 | 0 | 0.81 | 0.69 | 0.20 | 0.1 | 0.38 | 0.48 | 0.14 |
| 5.5 | 0.06 | 0 | 0.94 | 0.08 | 0 | 0.91 | 0.72 | 0.18 | 0.1 | 0.56 | 0.32 | 0.12 |
| 6 | 0.05 | 0 | 0.94 | 0.08 | 0 | 0.92 | 0.75 | 0.14 | 0.1 | 0.71 | 0.18 | 0.11 |
| 6.5 | 0.05 | 0 | 0.95 | 0.07 | 0 | 0.92 | 0.76 | 0.14 | 0.1 | 0.74 | 0.16 | 0.1 |
| 7 | 0.04 | 0 | 0.96 | 0.07 | 0 | 0.93 | 0.79 | 0.11 | 0.1 | 0.75 | 0.164 | 0.09 |
| 7.5 | 0.04 | 0 | 0.96 | 0.07 | 0 | 0.93 | 0.8 | 0.1 | 0.1 | 0.76 | 0.155 | 0.08 |
| 8 | 0.03 | 0 | 0.96 | 0.06 | 0 | 0.93 | 0.8 | 0.1 | 0.1 | 0.77 | 0.15 | 0.08 |
| 8.5 | 0.03 | 0 | 0.96 | 0.06 | 0 | 0.93 | 0.8 | 0.1 | 0.1 | 0.8 | 0.125 | 0.07 |
| 9 | 0.03 | 0 | 0.97 | 0.06 | 0 | 0.94 | 0.8 | 0.1 | 0.1 | 0.86 | 0.07 | 0.07 |
| 9.5 | 0.02 | 0 | 0.97 | 0.06 | 0 | 0.94 | 0.8 | 0.1 | 0.1 | 0.92 | 0.06 | 0.02 |
| 10 | 0.02 | 0 | 0.98 | 0.06 | 0 | 0.94 | 0.79 | 0.11 | 0.1 | 0.95 | 0.03 | 0.02 |
| 10.5 | 0.02 | 0 | 0.98 | 0.06 | 0 | 0.94 | 0.79 | 0.11 | 0.1 | 0.96 | 0.02 | 0.02 |
| 11 | 0.02 | 0 | 0.98 | 0.06 | 0 | 0.94 | 0.77 | 0.13 | 0.1 | 0.99 | 0.007 | 0.02 |
| 11.5 | 0.02 | 0 | 0.98 | 0.06 | 0 | 0.94 | 0.76 | 0.14 | 0.1 | 0.98 | 0 | 0.02 |
| 12 | 0.02 | 0 | 0.98 | 0.05 | 0 | 0.94 | 0.75 | 0.15 | 0.1 | 0.97 | 0.01 | 0.02 |
| 12.5 | 0.02 | 0 | 0.98 | 0.05 | 0 | 0.94 | 0.74 | 0.16 | 0.1 | 0.95 | 0.03 | 0.02 |
| 13 | 0.02 | 0 | 0.98 | 0.05 | 0 | 0.94 | 0.73 | 0.17 | 0.1 | 0.91 | 0.08 | 0.01 |
| 13.5 | 0.02 | 0 | 0.98 | 0.05 | 0 | 0.94 | 0.72 | 0.18 | 0.1 | 0.87 | 0.12 | 0.01 |
| 14 | 0.02 | 0 | 0.98 | 0.05 | 0 | 0.95 | 0.71 | 0.19 | 0.1 | 0.79 | 0.2 | 0.01 |
| 14.5 | 0.02 | 0 | 0.98 | 0.05 | 0 | 0.95 | 0.7 | 0.2 | 0.1 | 0.65 | 0.34 | 0.01 |

TABLE 5

Measured contrast in the integral regime - The contrast measured between integral radiation for a dressed human subject in the presence of a foreign object and in the absence of the foreign object for various combinations of clothes and foreign objects.

| | Components of the structure | | Radiant Flow |
|---|---|---|---|
| Radiator | Foreign object | Clothes | Contrast (%) |
| 1} Human body | 1) Segment of steel pipe D = 60 mm, L = 300 mm, thickness d = 5 mm. | 1] Sport-shirt, jumper (hosiery) | 72% |
| 1} | 2) Steel disc, D = 155 mm, d = 2 mm. | 1] | 57% |
| 1} | 3) Ruler (white plastic), 300 × 30 × 2 mm. | 1] | 11% |
| 1} | 4) Hand-hold multi-meter Escort EDM-1111A, yellow colored plastic case, 170 × 90 × 40 mm | 1] | 67% |
| 1} | 5) Segment of plastic pipe D = 30 mm, L = 250 mm, d = 0.5 mm. | 1] | 26% |
| 1} | 2) | 2] Underwear-shirt, shirt, jumper-hosiery, jacket-hosiery. | 36% |
| 1} | 4) | 2] | 50% |
| 1} | 6) Iron thin sheet - fold wrapped three times in white polyethylene packet thickness 3 × 0.3 mm | 3] Underwear shirt, shirt, jumper, winter jacket-hosiery, layered and silk-lined | 45% |
| 1} | 2) | 3] | 70% |
| 1} | 7) Rectangular plate, brown plastic (polyester), 150 × 150 × 4 mm | 3] | −22% |
| 1} | 4) | 3] | 80% |
| 1} | 8) Electronic calculator, black plastic case, 140 × 90 × 50 mm | 4] Underwear shirt, shirt, jumper, winter jacket-black natural leather, layered and silk-lined | 35% |
| 1} | S12) Explosive material, tablet TNT of diameter D = 40 mm, and of thickness d = 20 mm. | 1] | −30% |
| 2} Human palm | S3) Plastic (red PVC) disc D = 60 mm, d = 1 mm | 5] Shred of clothes (cream col. hosiery) | 20% |
| 2} | S4) Plastic (yellow polyester) disc D = 60 mm, d = 1.8 mm. | 5] | −4% |
| 2} | S5) Plastic (green polyethylene) disc D = 60 mm, d = 1.0 mm. | 5] | 30% |
| 2} | S6) Plastic (transparent polyethylene) disc D = 60 mm, d = 1.0 mm. | 5] | 21% |
| 2} | S7) Plastic (white polyester) disc D = 60 mm, d = 1.0 mm | 5] | 29% |
| 2} | S8) Plastic (brown polyester) disc D = 60 mm, d = 5.4 mm. | 5] | 21% |
| 2} | S9) Natural gray suede disc D = 60 mm, d = 1.5 mm. | 5] | −2.5% |
| 2} | S10) Black rubber disc D = 60 mm, d = 2.5 mm. | 5] | 16% |
| 2} | S11) Artificial black suede on textile disc, D = 60 mm d = 1.0 mm | 5] | −3% at edge +4% in middle |
| 2} | S10a) Porous black rubber disc D = 60 mm, d = 2.8 mm | 5] | 16% |

TABLE 6

Components of PM investigated in spectral regime - A list of physical models (clothes and foreign objects) tested in the spectral regime (results reported in FIG. 5-FIG. 12).

| Number of Model | Name of PM-components | | |
| --- | --- | --- | --- |
| | Radiator | Object | Clothes |
| 1 | Human skin | Aluminum | Hosiery: (yellow) |
| 2 | Human skin | Iron | (blue) |
| 3 | Human skin | Plastic | (red) |
| 4 | Human skin | Aluminum | Flax |
| 5 | Human skin | Iron | Silk (cream) |
| 6 | Human skin | Plastic | Flax |
| 7 | Human skin | Aluminum | Silk (cream) |
| 8 | Human skin | MgO | Hosiery (yellow) |
| 9 | Human skin | Plastic | Silk (cream) |
| 10 | Human skin | MgO | Silk (cream) |
| 11 | Human skin | Aluminum | MgO |

What is claimed is:

1. A method for identifying a foreign object in proximity to a living tissue, comprising the steps of:
   a) finding a location of an anomaly in a radiation emitted by the living tissue, said anomaly caused by the foreign object;
   b) performing a spectral scan substantially only of a signal emanated from said location; and
   c) identifying the foreign object based on said location and a result of said spectral scan.

2. The method of claim 1, wherein said radiation includes energy in a frequency band between 5 and 7 μm.

3. The method of claim 2, where said frequency band includes a wide range of wavelengths spanning from a minimum wavelength of less than 5 μm till a maximum wavelength of greater than 12 μm.

4. The method of claim 1, wherein said radiation includes energy in a first infrared frequency band having wavelength less than 7 μm and said radiation also includes energy in a second frequency band having wavelength greater than 14 μm.

5. The method of claim 1, further including the step of:
   d) calculating a differential measure to quantify a level of said radiation at said location.

6. The method of claim 5, wherein said step of calculating includes quantifying a difference between a background level of said radiation and said level of said radiation at said location.

7. The method of claim 5, wherein said differential measure is a contrast.

8. The method of claim 1, further including the steps:
   d) classifying the foreign object to a general category based on a characteristic of said anomaly, and
   e) adapting said spectral scan to distinguish amongst objects in said general category.

9. The method of claim 8, wherein said characteristic is a contrast between a level of said radiation measured at said location and a background level of said radiation emitted by the living tissue effectively unmodified by the foreign object.

10. The method of claim 9, wherein said step of classifying is according to a sign and a magnitude of said contrast.

11. The method of claim 8, wherein said step of adapting includes choosing a frequency band for said spectral scan, said frequency band being optimal for distinguishing between at least two objects in said general category.

12. The method of claim 1, wherein said radiation is in a first frequency band and said step of performing said spectral scan includes the substeps:
   (i) evaluating a background level in a second frequency band said second frequency band being different from said first frequency band,
   (ii) measuring a level of said signal emanated from said location in said second frequency band,
   (iii) calculating a contrast between said background level and said level of said signal.

13. The method of claim 1, wherein said signal includes at least one emanation selected from the group consisting of said radiation modified by the foreign object; an output of an external radiation source, said output interacting with the foreign object; a heat flow from the living tissue; a heat flow from the foreign object.

* * * * *